United States Patent [19]
Avraham et al.

[11] Patent Number: 6,066,451
[45] Date of Patent: May 23, 2000

[54] NEURAL CELL PROTEIN MARKER RR/B AND DNA ENCODING THE SAME

[75] Inventors: Shalom Avraham; Hava Avraham; Jerome E. Groopman, all of Brookline, Mass.

[73] Assignee: Beth Israel Deaconess Medical Center, Inc., Boston, Mass.

[21] Appl. No.: 08/862,508

[22] Filed: May 23, 1997

Related U.S. Application Data

[62] Division of application No. 08/317,305, Oct. 3, 1994.
[51] Int. Cl.[7] .............................. C12Q 1/68; C07H 21/04
[52] U.S. Cl. ............................ 435/6; 536/23.5; 435/69.1; 435/320.1; 435/325; 435/252.3
[58] Field of Search ........................... 435/6, 69.1, 320.1, 435/325, 252.3; 536/23.5, 24.3, 24.31, 24.33

[56] References Cited

FOREIGN PATENT DOCUMENTS 9316178  8/1993  WIPO .

OTHER PUBLICATIONS

Adams et al. Nature Genetics, 4:256–267, 1993.
Adams, M. et al., "3,400 New Expressed Sequence Tags Identify Diversity of Transcripts in Human Brain", *Nature Genetics*, vol. 4, pp. 256–267 (1993).
Arnheiter, H. et al., "Physicochemical and Antigenic Properties of Synthetic Fragments of Human Leukocyte Interferon", *Nature*, vol. 294, pp. 278–280 (1981).
Bantle, J. et al., "Complexity and Characterization of Polyadenylated RNA in the Mouse Brain", *Cell*, vol. 8, pp. 139–150 (1976).
Guillemin, R., "Peptides in the Brain: The New Endocrinology of the Neuron", *Science*, vol. 202, pp. 390–402 (1978).
Hastie, N. et al., "The Expression of Three Abundance Classes of Messenger RNA in Mouse Tissues", *Cell*, vol. 9, pp. 761–774 (1976).
Purves, D. et al.,*Principles of Neural Development*, Publised by Sinauer Associates Inc., pp. 263–267 (1985).
Sambrook, J. et al.,*Molecular Cloning*, A Laboratory Manual, Published by Cold Spring Harbor Laboratory Press, Chapter 16, pp. 16.2–16.81 (1989).

*Primary Examiner*—Patricia Duffy
*Attorney, Agent, or Firm*—Lahive & Cockfield, LLP

[57] ABSTRACT

The invention contemplates the novel neural cell protein marker RR/B, cDNA encoding RR/B, nucleic acid probes for detection of mRNA encoding RR/B, synthetic polypeptides whose sequences correspond to a portion of RR/B and have a molecular weight equal to less than that of RR/B antibodies specific for RR/B, and methods for detection of RR/B.

8 Claims, 19 Drawing Sheets

```
ATGTCAGTCAGTGTGCATGAGAACCGCAAGTCCAGGGCCAGCAGCGGCTCCATTAACATCTATCT
GTTTCACAAGTCCTCCTACGCTGACAGCGTCCTCACTCACCTGAATCTTTTACGCCAGCAGCGTC
TCTTCACTGACGTCCTTCTCCATGCCGGAAATAGGACCTTCCCTTGCCACCGGGCAGTGCTGGCT
GCATGCAGTCGCTACTTTGAGGCATGTTCAGTGGTGGCCTGAAAGAGAGCCAGGACAGTGAGGT
CAACTTTGACAATTCCATCCACCCAGAAGTCTTGGAGCTGCTGCTTGACTATGCGTACTCCTCCC
GGGTCATCATCAATGAAGAAATGCAGAATCGCTCCTGGAAGCTGGTGACATGCTGGAGTTTCAA
GACATCCGGGATGCATGTGCAGAGTTCCTGGAAAAGAACCTGCATCCCACCAACTGCCTGGGCAT
GCTGCTGCTGTCTGATGCACACCAGTGCACCAAGCTGTACGAACTATCTTGGAGAATGTGTCTCA
GCAACTTCCAAACCATCAGGAAGAATGAAGATTTCCTCCAGCTGCCCCAGGACATGGTAGTGCAA
CTCTTGTCCAGTGAAGAGCTGGAGACAGAGGATGAAAGGCTTGTGTACGAGTCTGCAATTAACTG
GATCAGCTATGACCTGAAGAAGCGCTATTGCTACCTCCCAGAACTGTTGCAGACAGTAAGGCTGG
CACTTCTGCCAGCCATCTATCTCATGGAGAATGTGGCCATGGAGGAACTCATCACCAAGCAGAGA
AAGAGTAAGGAAATTGTGGAAGAGGCCATCAGGTGCAAACTGAAAATCCTGCAGAATGACGGTGT
GGTAACCAGCCTCTGTGCCCGACCTCGGAAAACTGGCCATGCCCTCTTCCTTCTGGGAGGACAGA
CTTTCATGTGTGACAAGTTGTATCTGGTAGACCAGAAGGCCAAAGAAATCATTCCCAAGGCTGAC
ATTCCCAGCCCAAGAAAAGAGTTTAGTGCATGTGCGATTGGCTGCAAAGTGTACATTACTGGGGG
GCGGGGGTCTGAAAATGGGGTCTCGAAAGATGTCTGGGTTTATGATACCCTGCACGAGGAGTGGT
CCAAGGCTGCCCCCATGCTGGTGGCCAGGTTTGGCCATGGCTCTGCTGAACTGAAGCACTGCCTG
TATGTGGTTGGGGGGCACACGGCCGCAACTGGCTGCCTCCCGGCCTCCCCCTCAGTCTCTCTAAA
GCAGGTAGAACATTATGACCCCACAATCAACAAATGGACCATGGTGGCCCCACTCCGAGAAGGCG
TTAGCAACGCCGCAGTAGTGAGTGCCAAACTTAAGTTATTTGCTTTCGGAGGTACCAGTGTCAGT
CATGACAAGCTCCCCAAAGTTCAGTGTTACGATCAGTGTGAAAACAGGTGGACTGTACCGGCCAC
CTGTCCCCAGCCCTGGCGTTACACAGCAGCAGCTGTGCTGGGGAACCAGATTTTTATTATGGGGG
GTGATACAGAATTCTCTGCCTGCTCTGCTTATAAATTCAACAGTGAGACTTACCAGTGGACCAAA
```

FIG. 1A

GTGGGAGATGTGACAGCAAAGCGCATGAGCTGCCATGCTGTGGCCTCTGGAAACAAACTCTACGT

GGTTGGAGGATACTTTGGCATTCAGCGATGCAAGACTTTGGACTGCTACGATCCAACATTAGACG

TGTGGAACAGCATCACCACTGTCCCGTACTCGCTGATTCCTACTGCATTTGTCAGCACCTGGAAA

CATCTGCCTTCTTAA

FIG. 1A (con't)

MSVSVHENRKSRASSGSINIYLFHKSSYADSVLTHLNLLRQQRLFTDVLLHAGNRTFPCH

RAVLAACSRYFEAMFSGGLKESQDSEVNFDNSIHPEVLELLLDYAYSSRVIINEENAESL

LEAGDMLEFQDIRDACAEFLEKNLHPTNCLGMLLLSDAHQCTKLYELSWRMCLSNFQTIR

KNEDFLQLPQDMVVQLLSSEELETEDERLVYESAMNWISYDLKKRYCYLPELLQTVRLAL

LPAIYLMENVAMEELITKQRKSKEIVEEAIRCKLKILQNDGVVTSLCARPRKTGHALFLL

GGQTFMCDKLYLVDQKAKEIIPKADIPSPRKEFSACAIGCKVYITGGRGSENGVSKDVWV

YDTLHEEWSKAAPMLVARFGHGSAELKHCLYVVGGHTAATGCLPASPSVSLKQVEQYDPT

TNKWTMVAPLREGVSNAAVVSAKLKLFAFGGTSVSHDKLPKVQCYDQCENRWSVPATCPQ

PWRYTAAAVLGNQIFIMGGDTEFSACSAYKFNSETYQWTKVGDVTAKRMSCHAVASGNKL

YVVGGYFGIQRCKTLDCYDPTLDVWNSITTVPYSLIPTAFVSTWKHLPS

FIG. 1B

```
ATGTCAGTCAGTGTGCATGAGAACCGCAAGTCCAGGGCCAGCAGTGGCTCCATCAACATCTACCT
GTTTCATAAGTCCTCCTACGCGGACAGCGTTCTCACTCACCTGAACCTTCTGCGTCAGCAGCGGC
TCTTCACAGATGTCCTTCTCCATGCGGGAAACAGGACCTTCCCTTGCCACCGGGCAGTGCTGGCT
GCGTGCAGCCGCTACTTCGAAGCCATGTTCAGTGGTGGCCTGAAAGAGAGCCAGGACAGTGAGGT
GAACTTCGACAATTCCATCCACCCAGAAGTCTTAGAGCTGCTTCTAGACTACGCATACTCCTCCC
GGGTCATTATCAATGAAGAAATGCTGAGTCGCTCCTGGAGGCTGGTGACATGCTGGAGTTCCAG
GACATCAGAGATGCGTGTGCAGAATTTCTAGAGAAGAACCTGCATCCCACCAACTGCCTGGGTAT
GCTGCTGTTGTCTGATGCCCACCAGTGCACCAAGCTGTACGAACTCTCCTGGAGAATGTGTCTCA
GCAACTTCCAAACCATTCGGAAGAACGAAGATTTCCTCCAGTTGCCCCAGGACATGGTTGTGCAG
CTGCTGTCCAGTGAAGAACTGGAGACGGAAGACGAAAGGCTGGTGTATGAGTCTGCGATGAACTG
GATCAGCTATGACCTGAAGAAGCGCTACTGTTACCTCCCGGAACTGTTGCAGACAGTGAGGCTGG
CCCTCCTTCCTGCCATCTATCTCATGGAGAACGTGGCGATGGAAGAACTCATCACCAAGCAGAGA
AAGAGTAAGGAGATCGTGGAAGAGGCCATCAGGTGCAAACTAAAAATCTTACAGAATGACGGCGT
GGTCACCAGTCTCTGTGCTCGTCCTCGGAAAACTGGCCATGCCCTGTTCCTCCTGGGAGGGCAGA
CTTTCATGTGTGACAAACTGTACTTGGTAGACCAGAAGGCTAAAGAAATCATTCCCAAGGCTGAC
ATTCCCAGCCCGAGGAAGAGTTCAGCGCATGTGCAATTGGCTGCAAAGTATATATTACTGGGGG
GCGGGGATCAGAGAACGGAGTCTCAAAAGATGTCTGGGTTTACGATACCCTGCATGAGGAGTGGT
CCAAGGCTGCCCCCATGCTGGTGGCCAGGTTTGGCCATGGATCTGCTGAACTGAAGCACTGCCTC
TATGTAGTCGGTGGGCACACAGCTGCAACTGGCTGCCTCCCAGCCTCCCCCTCGGTCTCCCTAAA
GCAAGTAGAACAGTATGACCCCACAACCAACAAATGGACCATGGTAGCCCCACTCCGCGAAGGTG
TCAGCAATGCTGCTGTAGTGAGTGCCAAACTTAAGCTGTTTGCTTTCGGGGGTACCAGTGTGAGC
CACGACAAGCTGCCCAAGGTTCAGTGTTACGATCAATGCGAGAACAGATGGTCAGTGCCGGCCAC
CTGTCCCCAGCCCTGGCGTTACACAGCCGCAGCTGTGCTGGGAAACCAGATTTTTATCATGGGTG
GAGATACAGAGTTCTCTGCCTGCTCCGCTTACAAATTCAATAGTGAGACTTACCAGTGGACCAAG
```

FIG. 2

GTGGGAGATGTGACAGCCAAGCGCATGAGCTGCCACGCCGTGGCGTCCGGGAACAAGCTTTACGT

AGTTGGAGGGTACTTCGGCATTCAGCGCTGCAAGACTTTGGACTGTTACGACCCAACTTTAGATG

TGTGGAACAGCATAACCACTGTTCCCTACTCTCTGATCCCTACTGCATTCGTCAGCACCTGGAAA

CACCTGCCTTCCTAA

FIG. 2 (con't)

MSVSVHENRKSRASSGSINIYLFHKSSYADSVLTHLNLLRQQRLFTDVLLHAGNRTFPCH

RAVLAACSRYFEAMFSGGLKESQDSEVNFDNSIHPEVLELLLDYAYSSRVIINEENAESL

LEAGDMLEFQDIRDACAEFLEKNLHPTNCLGMLLLSDAHQCTKLYELSWRMCLSNFQTIR

KNEDFLQLPQDMVVQLLSSEELETEDERLVYESAINWISYDLKKRYCYLPELLQTVRLAL

LPAIYLMENVAMEELITKQRKSKEIVEEAIRCKLKILQNDGVVTSLCARPRKTGHALFLL

GGQTFMCDKLYLVDQKAKEIIPKADIPSPRKEFSACAIGCKVYITGGRGSENGVSKDVWV

YDTLHEEWSKAAPMLVARFGHGSAELKHCLYVVGGHTAATGCLPASPSVSLKQVEHYDPT

INKWTMVAPLREGVSNAAVVSAKLKLFAFGGTSVSHDKLPKVQCYDQCENRWTVPATCPQ

PWRYTAAAVLGNQIFIMGGDTEFSACSAYKFNSETYQWTKVGDVTAKRMSCHAVASGNKL

YVVGGYFGIQRCKTLDCYDPTLDVWNSITTVPYSLIPTAFVSTWKHLPS

FIG. 3

```
                    1                                                        39
Human       ATGTCAGTC AGTGTGCATG AGAACCGCAA GTCCAGGGCC
Mouse       ATGTCAGTC AGTGTGCATG AGAACCGCAA GTCCAGGGCC
Consensus   ATGTCAGTC AGTGTGCATG AGAACCGCAA GTCCAGGGCC 40                                                                89
AGCAGCGGCT CCATTAACAT CTATCTGTTT CACAAGTCCT CCTACGCTGA
AGCAGTGGCT CCATCAACAT CTACCTGTTT CATAAGTCCT CCTACGCGGA
AGCAG-GGCT CCAT-AACAT CTA-CTGTTT CA-AAGTCCT CCTACGC-GA 90                                                               139
CAGCGTCCTC ACTCACCTGA ATCTTTTACG CCAGCAGCGT CTCTTCACTG
CAGCGTTCTC ACTCACCTGA ACCTTCTGCG TCAGCAGCGG CTCTTCACAG
CAGCGT-CTC ACTCACCTGA A-CTT-T-CG -CAGCAGCG- CTCTTCAC-G 140                                                              189
ACGTCCTTCT CCATGCCGGA AATAGGACCT TCCCTTGCCA CCGGGCAGTG
ATGTCCTTCT CCATGCGGGA AACAGGACCT TCCCTTGCCA CCGGGCAGTG
A-GTCCTTCT CCATGC-GGA AA-AGGACCT TCCCTTGCCA CCGGGCAGTG 190                                                              239
CTGGCTGCAT GCAGTCGCTA CTTTGAGGCC ATGTTCAGTG GTGGCCTGAA
CTGGCTGCGT GCAGCCGCTA CTTCGAAGCC ATGTTCAGTG GTGGCCTGAA
CTGGCTGC-T GCAG-CGCTA CTT-GA-GCC ATGTTCAGTG GTGGCCTGAA 240                                                              289
AGAGAGCCAG GACAGTGAGG TCAACTTTGA CAATTCCATC CACCCAGAAG
AGAGAGCCAG GACAGTGAGG TGAACTTCGA CAATTCCATC CACCCAGAAG
AGAGAGCCAG GACAGTGAGG T-AACTT-GA CAATTCCATC CACCCAGAAG 290                                                              339
TCTTGGAGCT GCTGCTTGAC TATGCGTACT CCTCCCGGGT CATCATCAAT
TCTTAGAGCT GCTTCTAGAC TACGCATACT CCTCCCGGGT CATTATCAAT
TCTT-GAGCT GCT-CT-GAC TA-GC-TACT CCTCCCGGGT CAT-ATCAAT 340                                                              389
GAAGAAAATG CAGAATCGCT CCTGGAAGCT GGTGACATGC TGGAGTTTCA
GAAGAAAATG CTGAGTCGCT CCTGGAGGCT GGTGACATGC TGGAGTTCCA
GAAGAAAATG C-GA-TCGCT CCTGGA-GCT GGTGACATGC TGGAGTT-CA 390                                                              439
AGACATCCGG GATGCATGTG CAGAGTTCCT GGAAAAGAAC CTGCATCCCA
GGACATCAGA GATGCGTGTG CAGAATTTCT AGAGAAGAAC CTGCATCCCA
-GACATC-G- GATGC-TGTG CAGA-TT-CT -GA-AAGAAC CTGCATCCCA 440                                                              489
CCAACTGCCT GGGCATGCTG CTGCTGTCTG ATGCACACCA GTGCACCAAG
CCAACTGCCT GGGTATGCTG CTGTTGTCTG ATGCCCACCA GTGCACCAAG
CCAACTGCCT GGG-ATGCTG CTG-TGTCTG ATGC-CACCA GTGCACCAAG
```

FIG. 4

```
490                                                                   539
CTGTACGAAC TATCTTGGAG AATGTGTCTC AGCAACTTCC AAACCATCAG
CTGTACGAAC TCTCCTGGAG AATGTGTCTC AGCAACTTCC AAACCATTCG
CTGTACGAAC T-TC-TGGAG AATGTGTCTC AGCAACTTCC AAACCAT--G 540                                                                   589
GAAGAATGAA GATTTCCTCC AGCTGCCCCA GGACATGGTA GTGCAACTCT
GAAGAACGAA GATTTCCTCC AGTTGCCCCA GGACATGGTT GTGCAGCTGC
GAAGAA-GAA GATTTCCTCC AG-TGCCCCA GGACATGGT- GTGCA-CT--

590                                                                   639
TGTCCAGTGA AGAGCTGGAG ACAGAGGATG AAAGGCTTGT GTACGAGTCT
TGTCCAGTGA AGAACTGGAG ACGGAAGACG AAAGGCTGGT GTATGAGTCT
TGTCCAGTGA AGA-CTGGAG AC-GA-GA-G AAAGGCT-GT GTA-GAGTCT 640                                                                   689
GCAATTAACT GGATCAGCTA TGACCTGAAG AAGCGCTATT GCTACCTCCC
GCGATGAACT GGATCAGCTA TGACCTGAAG AAGCGCTACT GTTACCTCCC
GC-AT-AACT GGATCAGCTA TGACCTGAAG AAGCGCTA-T G-TACCTCCC 690                                                                   739
AGAACTGTTG CAGACAGTAA GGCTGGCACT TCTGCCAGCC ATCTATCTCA
GGAACTGTTG CAGACAGTGA GGCTGGCCCT CCTTCCTGCC ATCTATCTCA
-GAACTGTTG CAGACAGT-A GGCTGGC-CT -CT-CC-GCC ATCTATCTCA 740                                                                   789
TGGAGAATGT GGCCATGGAG GAACTCATCA CCAAGCAGAG AAAGAGTAAG
TGGAGAACGT GGCGATGGAA GAACTCATCA CCAAGCAGAG AAAGAGTAAG
TGGAGAA-GT GGC-ATGGA- GAACTCATCA CCAAGCAGAG AAAGAGTAAG 790                                                                   839
GAAATTGTGG AAGAGGCCAT CAGGTGCAAA CTGAAAATCC TGCAGAATGA
GAGATCGTGG AAGAGGCCAT CAGGTGCAAA CTAAAAATCT TACAGAATGA
GA-AT-GTGG AAGAGGCCAT CAGGTGCAAA CT-AAAATC- T-CAGAATGA 840                                                                   889
CGGTGTGGTA ACCAGCCTCT GTGCCCGACC TCGGAAAACT GGCCATGCCC
CGGCGTGGTC ACCAGTCTCT GTGCTCGTCC TCGGAAAACT GGCCATGCCC
CGG-GTGGT- ACCAG-CTCT GTGC-CG-CC TCGGAAAACT GGCCATGCCC 890                                                                   939
TCTTCCTTCT GGGAGGACAG ACTTTCATGT GTGACAAGTT GTATCTGGTA
TGTTCCTCCT GGGAGGGCAG ACTTTCATGT GTGACAAACT GTACTTGGTA
T-TTCCT-CT GGGAGG-CAG ACTTTCATGT GTGACAA--T GTA--TGGTA 940                                                                   989
GACCAGAAGG CCAAAGAAAT CATTCCCAAG GCTGACATTC CCAGCCCAAG
GACCAGAAGG CTAAAGAAAT CATTCCCAAG GCTGACATTC CCAGCCCGAG
GACCAGAAGG C-AAAGAAAT CATTCCCAAG GCTGACATTC CCAGCCC-AG
```

FIG. 4 (con't)

```
990                                                               1039
AAAAGAGTTT AGTGCATGTG CGATTGGCTG CAAAGTGTAC ATTACTGGGG
GAAAGAGTTC AGCGCATGTG CAATTGGCTG CAAAGTATAT ATTACTGGGG
-AAAGAGTT- AG-GCATGTG C-ATTGGCTG CAAAGT-TA- ATTACTGGGG 1040                                                              1089
GGCGGGGGTC TGAAAATGGG GTCTCGAAAG ATGTCTGGGT TTATGATACC
GGCGGGGATC AGAGAACGGA GTCTCAAAAG ATGTCTGGGT TTACGATACC
GGCGGGG-TC -GA-AA-GG- GTCTC-AAAG ATGTCTGGGT TTA-GATACC 1090                                                              1139
CTGCACGAGG AGTGGTCCAA GGCTGCCCCC ATGCTGGTGG CCAGGTTTGG
CTGCATGAGG AGTGGTCCAA GGCTGCCCCC ATGCTGGTGG CCAGGTTTGG
CTGCA-GAGG AGTGGTCCAA GGCTGCCCCC ATGCTGGTGG CCAGGTTTGG 1140                                                              1189
CCATGGCTCT GCTGAACTGA AGCACTGCCT GTATGTGGTT GGGGGGCACA
CCATGGATCT GCTGAACTGA AGCACTGCCT CTATGTAGTC GGTGGGCACA
CCATGG-TCT GCTGAACTGA AGCACTGCCT -TATGT-GT- GG-GGGCACA 1190                                                              1239
CGGCCGCAAC TGGCTGCCTC CCGGCCTCCC CCTCAGTCTC TCTAAAGCAG
CAGCTGCAAC TGGCTGCCTC CCAGCCTCCC CCTCGGTCTC CCTAAAGCAA
C-GC-GCAAC TGGCTGCCTC CC-GCCTCCC CCTC-GTCTC -CTAAAGCA- 1240                                                              1289
GTAGAACATT ATGACCCCAC AATCAACAAA TGGACCATGG TGGCCCCACT
GTAGAACAGT ATGACCCCAC AACCAACAAA TGGACCATGG TAGCCCCACT
GTAGAACA-T ATGACCCCAC AA-CAACAAA TGGACCATGG T-GCCCCACT 1290                                                              1339
CCGAGAAGGC GTTAGCAACG CCGCAGTAGT GAGTGCCAAA CTTAAGTTAT
CCGCGAAGGT GTCAGCAATG CTGCTGTAGT GAGTGCCAAA CTTAAGCTGT
CCG-GAAGG- GT-AGCAA-G C-GC-GTAGT GAGTGCCAAA CTTAAG-T-T 1340                                                              1389
TTGCTTTCGG AGGTACCAGT GTCAGTCATG ACAAGCTCCC CAAAGTTCAG
TTGCTTTCGG GGGTACCAGT GTGAGCCACG ACAAGCTGCC CAAGGTTCAG
TTGCTTTCGG -GGTACCAGT GT-AG-CA-G ACAAGCT-CC CAA-GTTCAG 1390                                                              1439
TGTTACGATC AGTGTGAAAA CAGGTGGACT GTACCGGCCA CCTGTCCCCA
TGTTACGATC AATGCGAGAA CAGATGGTCA GTGCCGGCCA CCTGTCCCCA
TGTTACGATC A-TG-GA-AA CAG-TGG-C- GT-CCGGCCA CCTGTCCCCA 1440                                                              1489
GCCCTGGCGT TACACAGCAG CAGCTGTGCT GGGGAACCAG ATTTTTATTA
GCCCTGGCGT TACACAGCCG CAGCTGTGCT GGGAAACCAG ATTTTTATCA
GCCCTGGCGT TACACAGC-G CAGCTGTGCT GGG-AACCAG ATTTTTAT-A
```

FIG. 4 (con't)

```
1490                                                                 1539
TGGGGGGTGA TACAGAATTC TCTGCCTGCT CTGCTTATAA ATTCAACAGT
TGGGTGGAGA TACAGAGTTC TCTGCCTGCT CCGCTTACAA ATTCAATAGT
TGGG-GG-GA TACAGA-TTC TCTGCCTGCT C-GCTTA-AA ATTCAA-AGT 1540                                                                 1589
GAGACTTACC AGTGGACCAA AGTGGGAGAT GTGACAGCAA AGCGCATGAG
GAGACTTACC AGTGGACCAA GGTGGGAGAT GTGACAGCCA AGCGCATGAG
GAGACTTACC AGTGGACCAA -GTGGGAGAT GTGACAGC-A AGCGCATGAG 1590                                                                 1639
CTGCCATGCT GTGGCCTCTG GAAACAAACT CTACGTGGTT GGAGGATACT
CTGCCACGCC GTGGCGTCCG GAACAAGCT TTACGTAGTT GGAGGGTACT
CTGCCA-GC- GTGGC-TC-G G-AACAA-CT -TACGT-GTT GGAGG-TACT 1640                                                                 1689
TTGGCATTCA GCGATGCAAG ACTTTGGACT GCTACGATCC AACATTAGAC
TCGGCATTCA GCGCTGCAAG ACTTTGGACT GTTACGACCC AACTTTAGAT
T-GGCATTCA GCG-TGCAAG ACTTTGGACT G-TACGA-CC AAC-TTAGA- 1690                                                                 1739
GTGTGGAACA GCATCACCAC TGTCCCGTAC TCGCTGATTC CTACTGCATT
GTGTGGAACA GCATAACCAC TGTTCCCTAC TCTCTGATCC CTACTGCATT
GTGTGGAACA GCAT-ACCAC TGT-CC-TAC TC-CTGAT-C CTACTGCATT 1740                                    1770
TGTCAGCACC TGGAAACATC TGCCTTCTTA A
CGTCAGCACC TGGAAACACC TGCCTTCCT. A
-GTCAGCACC TGGAAACA-C TGCCTTC-T- A
```

FIG. 4 (con't)

```
1                                                                               60
MSVSVHENRK  SRASSGSINI  YLFHKSSYAD  SVLTHLNLLR  QQRLFTDVLL  HAGNRTFPCH

MSVSVHENRK  SRASSGSINI  YLFHKSSYAD  SVLTHLNLLR  QQRLFTDVLL  HAGNRTFPCH 61                                                                              120
RAVLAACSRY  FEAMFSGGLK  ESQDSEVNFD  NSIHPEVLEL  LLDYAYSSRV  IINEENAESL

RAVLAACSRY  FEAMFSGGLK  ESQDSEVNFD  NSIHPEVLEL  LLDYAYSSRV  IINEENAESL 121                                                                             180
LEAGDMLEFQ  DIRDACAEFL  EKNLHPTNCL  GMLLLSDAHQ  CTKLYELSWR  MCLSNFQTIR

LEAGDMLEFQ  DIRDACAEFL  EKNLHPTNCL  GMLLLSDAHQ  CTKLYELSWR  MCLSNFQTIR 181                                                                             240
KNEDFLQLPQ  DMVVQLLSSE  ELETEDERLV  YESAINWISY  DLKKRYCYLP  ELLQTVRLAL

KNEDFLQLPQ  DMVVQLLSSE  ELETEDERLV  YESAMNWISY  DLKKRYCYLP  ELLQTVRLAL 241                                                                             300
LPAIYLMENV  AMEELITKQR  KSKEIVEEAI  RCKLKILQND  GVVTSLCARP  RKTGHALFLL

LPAIYLMENV  AMEELITKQR  KSKEIVEEAI  RCKLKILQND  GVVTSLCARP  RKTGHALFLL 301                                                                             360
GGQTFMCDKL  YLVDQKAKEI  IPKADIPSPR  KEFSACAIGC  KVYITGGRGS  ENGVSKDVWV

GGQTFMCDKL  YLVDQKAKEI  IPKADIPSPR  KEFSACAIGC  KVYITGGRGS  ENGVSKDVWV 361                                                                             420
YDTLHEEWSK  AAPMLVARFG  HGSAELKHCL  YVVGGHTAAT  GCLPASPSVS  LKQVEHYDPT

YDTLHEEWSK  AAPMLVARFG  HGSAELKHCL  YVVGGHTAAT  GCLPASPSVS  LKQVEQYDPT 421                                                                             480
INKWTMVAPL  REGVSNAAVV  SAKLKLFAFG  GTSVSHDKLP  KVQCYDQCEN  RWTVPATCPQ

TNKWTMVAPL  REGVSNAAVV  SAKLKLFAFG  GTSVSHDKLP  KVQCYDQCEN  RWSVPATCPQ
```

FIG. 5

```
481                                                                   540
PWRYTAAAVL GNQIFIMGGD TEFSACSAYK FNSETYQWTK VGDVTAKRMS CHAVASGNKL

PWRYTAAAVL GNQIFIMGGD TEFSACSAYK FNSETYQWTK VGDVTAKRMS CHAVASGNKL 541                                                590
YVVGGYFGIQ RCKTLDCYDP TLDVWNSITT VPYSLIPTAF VSTWKHLPS

YVVGGYFGIQ RCKTLDCYDP TLDVWNSITT VPYSLIPTAF VSTWKHLPS
```

FIG. 5 (con't)

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 1770 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1767

(xi) SEQUENCE DESCRIPTION: SEQ ID NO:1:

```
ATG TCA GTC AGT GTG CAT GAG AAC CGC AAG TCC AGG GCC AGC AGC GGC        48
Met Ser Val Ser Val His Glu Asn Arg Lys Ser Arg Ala Ser Ser Gly
 1               5                  10                  15

TCC ATT AAC ATC TAT CTG TTT CAC AAG TCC TCC TAC GCT GAC AGC GTC        96
Ser Ile Asn Ile Tyr Leu Phe His Lys Ser Ser Tyr Ala Asp Ser Val
                20                  25                  30

CTC ACT CAC CTG AAT CTT TTA CGC CAG CAG CGT CTC TTC ACT GAC GTC       144
Leu Thr His Leu Asn Leu Leu Arg Gln Gln Arg Leu Phe Thr Asp Val
            35                  40                  45

CTT CTC CAT GCC GGA AAT AGG ACC TTC CCT TGC CAC CGG GCA GTG CTG       192
Leu Leu His Ala Gly Asn Arg Thr Phe Pro Cys His Arg Ala Val Leu
        50                  55                  60
```

```
GCT GCA TGC AGT CGC TAC TTT GAG GCC ATG TTC AGT GGT GGC CTG AAA          240
Ala Ala Cys Ser Arg Tyr Phe Glu Ala Met Phe Ser Gly Gly Leu Lys
 65                  70                  75                  80

GAG AGC CAG GAC AGT GAG GTC AAC TTT GAC AAT TCC ATC CAC CCA GAA          288
Glu Ser Gln Asp Ser Glu Val Asn Phe Asp Asn Ser Ile His Pro Glu
                 85                  90                  95

GTC TTG GAG CTG CTG CTT GAC TAT GCG TAC TCC TCC CGG GTC ATC ATC          336
Val Leu Glu Leu Leu Leu Asp Tyr Ala Tyr Ser Ser Arg Val Ile Ile
            100                 105                 110

AAT GAA GAA AAT GCA GAA TCG CTC CTG GAA GCT GGT GAC ATG CTG GAG          384
Asn Glu Glu Asn Ala Glu Ser Leu Leu Glu Ala Gly Asp Met Leu Glu
        115                 120                 125

TTT CAA GAC ATC CGG GAT GCA TGT GCA GAG TTC CTG GAA AAG AAC CTG          432
Phe Gln Asp Ile Arg Asp Ala Cys Ala Glu Phe Leu Glu Lys Asn Leu
    130                 135                 140

CAT CCC ACC AAC TGC CTG GGC ATG CTG CTG CTG TCT GAT GCA CAC CAG          480
His Pro Thr Asn Cys Leu Gly Met Leu Leu Leu Ser Asp Ala His Gln
145                 150                 155                 160

TGC ACC AAG CTG TAC GAA CTA TCT TGG AGA ATG TGT CTC AGC AAC TTC          528
Cys Thr Lys Leu Tyr Glu Leu Ser Trp Arg Met Cys Leu Ser Asn Phe
                165                 170                 175

CAA ACC ATC AGG AAG AAT GAA GAT TTC CTC CAG CTG CCC CAG GAC ATG          576
Gln Thr Ile Arg Lys Asn Glu Asp Phe Leu Gln Leu Pro Gln Asp Met
            180                 185                 190

GTA GTG CAA CTC TTG TCC AGT GAA GAG CTG GAG ACA GAG GAT GAA AGG          624
Val Val Gln Leu Leu Ser Ser Glu Glu Leu Glu Thr Glu Asp Glu Arg
        195                 200                 205

CTT GTG TAC GAG TCT GCA ATT AAC TGG ATC AGC TAT GAC CTG AAG AAG          672
Leu Val Tyr Glu Ser Ala Ile Asn Trp Ile Ser Tyr Asp Leu Lys Lys
    210                 215                 220

CGC TAT TGC TAC CTC CCA GAA CTG TTG CAG ACA GTA AGG CTG GCA CTT          720
Arg Tyr Cys Tyr Leu Pro Glu Leu Leu Gln Thr Val Arg Leu Ala Leu
225                 230                 235                 240

CTG CCA GCC ATC TAT CTC ATG GAG AAT GTG GCC ATG GAG GAA CTC ATC          768
Leu Pro Ala Ile Tyr Leu Met Glu Asn Val Ala Met Glu Glu Leu Ile
                245                 250                 255

ACC AAG CAG AGA AAG AGT AAG GAA ATT GTG GAA GAG GCC ATC AGG TGC          816
Thr Lys Gln Arg Lys Ser Lys Glu Ile Val Glu Glu Ala Ile Arg Cys
            260                 265                 270

AAA CTG AAA ATC CTG CAG AAT GAC GGT GTG GTA ACC AGC CTC TGT GCC          864
Lys Leu Lys Ile Leu Gln Asn Asp Gly Val Val Thr Ser Leu Cys Ala
        275                 280                 285

CGA CCT CGG AAA ACT GGC CAT GCC CTC TTC CTT CTG GGA GGA CAG ACT          912
Arg Pro Arg Lys Thr Gly His Ala Leu Phe Leu Leu Gly Gly Gln Thr
    290                 295                 300

TTC ATG TGT GAC AAG TTG TAT CTG GTA GAC CAG AAG GCC AAA GAA ATC          960
Phe Met Cys Asp Lys Leu Tyr Leu Val Asp Gln Lys Ala Lys Glu Ile
305                 310                 315                 320

ATT CCC AAG GCT GAC ATT CCC AGC CCA AGA AAA GAG TTT AGT GCA TGT         1008
Ile Pro Lys Ala Asp Ile Pro Ser Pro Arg Lys Glu Phe Ser Ala Cys
                325                 330                 335

GCG ATT GGC TGC AAA GTG TAC ATT ACT GGG GGG CGG GGG TCT GAA AAT         1056
Ala Ile Gly Cys Lys Val Tyr Ile Thr Gly Gly Arg Gly Ser Glu Asn
            340                 345                 350

GGG GTC TCG AAA GAT GTC TGG GTT TAT GAT ACC CTG CAC GAG GAG TGG         1104
Gly Val Ser Lys Asp Val Trp Val Tyr Asp Thr Leu His Glu Glu Trp
        355                 360                 365
```

-continued

```
TCC AAG GCT GCC CCC ATG CTG GTG GCC AGG TTT GGC CAT GGC TCT GCT     1152
Ser Lys Ala Ala Pro Met Leu Val Ala Arg Phe Gly His Gly Ser Ala
    370                 375                 380

GAA CTG AAG CAC TGC CTG TAT GTG GTT GGG GGG CAC ACG GCC GCA ACT     1200
Glu Leu Lys His Cys Leu Tyr Val Val Gly Gly His Thr Ala Ala Thr
385                 390                 395                 400

GGC TGC CTC CCG GCC TCC CCC TCA GTC TCT CTA AAG CAG GTA GAA CAT     1248
Gly Cys Leu Pro Ala Ser Pro Ser Val Ser Leu Lys Gln Val Glu His
                405                 410                 415

TAT GAC CCC ACA ATC AAC AAA TGG ACC ATG GTG GCC CCA CTC CGA GAA     1296
Tyr Asp Pro Thr Ile Asn Lys Trp Thr Met Val Ala Pro Leu Arg Glu
            420                 425                 430

GGC GTT AGC AAC GCC GCA GTA GTG AGT GCC AAA CTT AAG TTA TTT GCT     1344
Gly Val Ser Asn Ala Ala Val Val Ser Ala Lys Leu Lys Leu Phe Ala
        435                 440                 445

TTC GGA GGT ACC AGT GTC AGT CAT GAC AAG CTC CCC AAA GTT CAG TGT     1392
Phe Gly Gly Thr Ser Val Ser His Asp Lys Leu Pro Lys Val Gln Cys
    450                 455                 460

TAC GAT CAG TGT GAA AAC AGG TGG ACT GTA CCG GCC ACC TGT CCC CAG     1440
Tyr Asp Gln Cys Glu Asn Arg Trp Thr Val Pro Ala Thr Cys Pro Gln
465                 470                 475                 480

CCC TGG CGT TAC ACA GCA GCA GCT GTG CTG GGG AAC CAG ATT TTT ATT     1488
Pro Trp Arg Tyr Thr Ala Ala Ala Val Leu Gly Asn Gln Ile Phe Ile
                485                 490                 495

ATG GGG GGT GAT ACA GAA TTC TCT GCC TGC TCT GCT TAT AAA TTC AAC     1536
Met Gly Gly Asp Thr Glu Phe Ser Ala Cys Ser Ala Tyr Lys Phe Asn
            500                 505                 510

AGT GAG ACT TAC CAG TGG ACC AAA GTG GGA GAT GTG ACA GCA AAG CGC     1584
Ser Glu Thr Tyr Gln Trp Thr Lys Val Gly Asp Val Thr Ala Lys Arg
        515                 520                 525

ATG AGC TGC CAT GCT GTG GCC TCT GGA AAC AAA CTC TAC GTG GTT GGA     1632
Met Ser Cys His Ala Val Ala Ser Gly Asn Lys Leu Tyr Val Val Gly
    530                 535                 540

GGA TAC TTT GGC ATT CAG CGA TGC AAG ACT TTG GAC TGC TAC GAT CCA     1680
Gly Tyr Phe Gly Ile Gln Arg Cys Lys Thr Leu Asp Cys Tyr Asp Pro
545                 550                 555                 560

ACA TTA GAC GTG TGG AAC AGC ATC ACC ACT GTC CCG TAC TCG CTG ATT     1728
Thr Leu Asp Val Trp Asn Ser Ile Thr Thr Val Pro Tyr Ser Leu Ile
                565                 570                 575

CCT ACT GCA TTT GTC AGC ACC TGG AAA CAT CTG CCT TCT TAA             1770
Pro Thr Ala Phe Val Ser Thr Trp Lys His Leu Pro Ser
            580                 585

(2) INFORMATION FOR SEQ ID NO:2:

(i) SEQUENCE CHARACTERISTICS:
        (A) LENGTH: 589 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Val Ser Val His Glu Asn Arg Lys Ser Arg Ala Ser Ser Gly
 1               5                  10                  15

Ser Ile Asn Ile Tyr Leu Phe His Lys Ser Ser Tyr Ala Asp Ser Val
            20                  25                  30

Leu Thr His Leu Asn Leu Leu Arg Gln Gln Arg Leu Phe Thr Asp Val
        35                  40                  45
```

-continued

```
Leu Leu His Ala Gly Asn Arg Thr Phe Pro Cys His Arg Ala Val Leu
     50                   55                  60

Ala Ala Cys Ser Arg Tyr Phe Glu Ala Met Phe Ser Gly Gly Leu Lys
 65              70                  75                      80

Glu Ser Gln Asp Ser Glu Val Asn Phe Asp Asn Ser Ile His Pro Glu
                 85                  90                  95

Val Leu Glu Leu Leu Leu Asp Tyr Ala Tyr Ser Ser Arg Val Ile Ile
            100                 105                 110

Asn Glu Glu Asn Ala Glu Ser Leu Leu Glu Ala Gly Asp Met Leu Glu
            115                 120                 125

Phe Gln Asp Ile Arg Asp Ala Cys Ala Glu Phe Leu Glu Lys Asn Leu
    130                 135                 140

His Pro Thr Asn Cys Leu Gly Met Leu Leu Ser Asp Ala His Gln
145                 150                 155                 160

Cys Thr Lys Leu Tyr Glu Leu Ser Trp Arg Met Cys Leu Ser Asn Phe
                165                 170                 175

Gln Thr Ile Arg Lys Asn Glu Asp Phe Leu Gln Leu Pro Gln Asp Met
            180                 185                 190

Val Val Gln Leu Leu Ser Ser Glu Glu Leu Glu Thr Glu Asp Glu Arg
            195                 200                 205

Leu Val Tyr Glu Ser Ala Ile Asn Trp Ile Ser Tyr Asp Leu Lys Lys
    210                 215                 220

Arg Tyr Cys Tyr Leu Pro Glu Leu Leu Gln Thr Val Arg Leu Ala Leu
225                 230                 235                 240

Leu Pro Ala Ile Tyr Leu Met Glu Asn Val Ala Met Glu Glu Leu Ile
                245                 250                 255

Thr Lys Gln Arg Lys Ser Lys Glu Ile Val Glu Glu Ala Ile Arg Cys
            260                 265                 270

Lys Leu Lys Ile Leu Gln Asn Asp Gly Val Val Thr Ser Leu Cys Ala
            275                 280                 285

Arg Pro Arg Lys Thr Gly His Ala Leu Phe Leu Leu Gly Gly Gln Thr
    290                 295                 300

Phe Met Cys Asp Lys Leu Tyr Leu Val Asp Gln Lys Ala Lys Glu Ile
305                 310                 315                 320

Ile Pro Lys Ala Asp Ile Pro Ser Pro Arg Lys Glu Phe Ser Ala Cys
                325                 330                 335

Ala Ile Gly Cys Lys Val Tyr Ile Thr Gly Gly Arg Gly Ser Glu Asn
            340                 345                 350

Gly Val Ser Lys Asp Val Trp Val Tyr Asp Thr Leu His Glu Glu Trp
            355                 360                 365

Ser Lys Ala Ala Pro Met Leu Val Ala Arg Phe Gly His Gly Ser Ala
    370                 375                 380

Glu Leu Lys His Cys Leu Tyr Val Val Gly Gly His Thr Ala Ala Thr
385                 390                 395                 400

Gly Cys Leu Pro Ala Ser Pro Ser Val Ser Leu Lys Gln Val Glu His
                405                 410                 415

Tyr Asp Pro Thr Ile Asn Lys Trp Thr Met Val Ala Pro Leu Arg Glu
            420                 425                 430

Gly Val Ser Asn Ala Ala Val Val Ser Ala Lys Leu Lys Leu Phe Ala
            435                 440                 445

Phe Gly Gly Thr Ser Val Ser His Asp Lys Leu Pro Lys Val Gln Cys
    450                 455                 460
```

```
Tyr Asp Gln Cys Glu Asn Arg Trp Thr Val Pro Ala Thr Cys Pro Gln
465                 470                 475                 480

Pro Trp Arg Tyr Thr Ala Ala Val Leu Gly Asn Gln Ile Phe Ile
            485                 490                 495

Met Gly Gly Asp Thr Glu Phe Ser Ala Cys Ser Ala Tyr Lys Phe Asn
                500                 505                 510

Ser Glu Thr Tyr Gln Trp Thr Lys Val Gly Asp Val Thr Ala Lys Arg
        515                 520                 525

Met Ser Cys His Ala Val Ala Ser Gly Asn Lys Leu Tyr Val Val Gly
        530                 535                 540

Gly Tyr Phe Gly Ile Gln Arg Cys Lys Thr Leu Asp Cys Tyr Asp Pro
545                 550                 555                 560

Thr Leu Asp Val Trp Asn Ser Ile Thr Thr Val Pro Tyr Ser Leu Ile
                565                 570                 575

Pro Thr Ala Phe Val Ser Thr Trp Lys His Leu Pro Ser
                580                 585
```

(2) INFORMATION FOR SEQ ID NO:3:

(i) SEQUENCE CHARACTERISTICS:
        (A) LENGTH: 1770 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1767

(xi) SEQUENCE DESCRIPTION: SEQ ID NO:3:

```
ATG TCA GTC AGT GTG CAT GAG AAC CGC AAG TCC AGG GCC AGC AGT GGC     48
Met Ser Val Ser Val His Glu Asn Arg Lys Ser Arg Ala Ser Ser Gly
1               5                   10                  15

TCC ATC AAC ATC TAC CTG TTT CAT AAG TCC TCC TAC GCG GAC AGC GTT     96
Ser Ile Asn Ile Tyr Leu Phe His Lys Ser Ser Tyr Ala Asp Ser Val
                20                  25                  30

CTC ACT CAC CTG AAC CTT CTG CGT CAG CAG CGG CTC TTC ACA GAT GTC    144
Leu Thr His Leu Asn Leu Leu Arg Gln Gln Arg Leu Phe Thr Asp Val
            35                  40                  45

CTT CTC CAT GCG GGA AAC AGG ACC TTC CCT TGC CAC CGG GCA GTG CTG    192
Leu Leu His Ala Gly Asn Arg Thr Phe Pro Cys His Arg Ala Val Leu
        50                  55                  60

GCT GCG TGC AGC CGC TAC TTC GAA GCC ATG TTC AGT GGT GGC CTG AAA    240
Ala Ala Cys Ser Arg Tyr Phe Glu Ala Met Phe Ser Gly Gly Leu Lys
65                  70                  75                  80

GAG AGC CAG GAC AGT GAG GTG AAC TTC GAC AAT TCC ATC CAC CCA GAA    288
Glu Ser Gln Asp Ser Glu Val Asn Phe Asp Asn Ser Ile His Pro Glu
                85                  90                  95

GTC TTA GAG CTG CTT CTA GAC TAC GCA TAC TCC TCC CGG GTC ATT ATC    336
Val Leu Glu Leu Leu Leu Asp Tyr Ala Tyr Ser Ser Arg Val Ile Ile
                100                 105                 110

AAT GAA GAA AAT GCT GAG TCG CTC CTG GAG GCT GGT GAC ATG CTG GAG    384
Asn Glu Glu Asn Ala Glu Ser Leu Leu Glu Ala Gly Asp Met Leu Glu
            115                 120                 125
```

```
TTC CAG GAC ATC AGA GAT GCG TGT GCA GAA TTT CTA GAG AAG AAC CTG          432
Phe Gln Asp Ile Arg Asp Ala Cys Ala Glu Phe Leu Glu Lys Asn Leu
        130                 135                 140

CAT CCC ACC AAC TGC CTG GGT ATG CTG CTG TTG TCT GAT GCC CAC CAG          480
His Pro Thr Asn Cys Leu Gly Met Leu Leu Leu Ser Asp Ala His Gln
145                 150                 155                 160

TGC ACC AAG CTG TAC GAA CTC TCC TGG AGA ATG TGT CTC AGC AAC TTC          528
Cys Thr Lys Leu Tyr Glu Leu Ser Trp Arg Met Cys Leu Ser Asn Phe
                165                 170                 175

CAA ACC ATT CGG AAG AAC GAA GAT TTC CTC CAG TTG CCC CAG GAC ATG          576
Gln Thr Ile Arg Lys Asn Glu Asp Phe Leu Gln Leu Pro Gln Asp Met
            180                 185                 190

GTT GTG CAG CTG CTG TCC AGT GAA GAA CTG GAG ACG GAA GAC GAA AGG          624
Val Val Gln Leu Leu Ser Ser Glu Glu Leu Glu Thr Glu Asp Glu Arg
                195                 200                 205

CTG GTG TAT GAG TCT GCG ATG AAC TGG ATC AGC TAT GAC CTG AAG AAG          672
Leu Val Tyr Glu Ser Ala Met Asn Trp Ile Ser Tyr Asp Leu Lys Lys
        210                 215                 220

CGC TAC TGT TAC CTC CCG GAA CTG TTG CAG ACA GTG AGG CTG GCC CTC          720
Arg Tyr Cys Tyr Leu Pro Glu Leu Leu Gln Thr Val Arg Leu Ala Leu
225                 230                 235                 240

CTT CCT GCC ATC TAT CTC ATG GAG AAC GTG GCG ATG GAA GAA CTC ATC          768
Leu Pro Ala Ile Tyr Leu Met Glu Asn Val Ala Met Glu Glu Leu Ile
                245                 250                 255

ACC AAG CAG AGA AAG AGT AAG GAG ATC GTG GAA GAG GCC ATC AGG TGC          816
Thr Lys Gln Arg Lys Ser Lys Glu Ile Val Glu Glu Ala Ile Arg Cys
            260                 265                 270

AAA CTA AAA ATC TTA CAG AAT GAC GGC GTG GTC ACC AGT CTC TGT GCT          864
Lys Leu Lys Ile Leu Gln Asn Asp Gly Val Val Thr Ser Leu Cys Ala
                275                 280                 285

CGT CCT CGG AAA ACT GGC CAT GCC CTG TTC CTC CTG GGA GGG CAG ACT          912
Arg Pro Arg Lys Thr Gly His Ala Leu Phe Leu Leu Gly Gly Gln Thr
        290                 295                 300

TTC ATG TGT GAC AAA CTG TAC TTG GTA GAC CAG AAG GCT AAA GAA ATC          960
Phe Met Cys Asp Lys Leu Tyr Leu Val Asp Gln Lys Ala Lys Glu Ile
305                 310                 315                 320

ATT CCC AAG GCT GAC ATT CCC AGC CCG AGG AAA GAG TTC AGC GCA TGT         1008
Ile Pro Lys Ala Asp Ile Pro Ser Pro Arg Lys Glu Phe Ser Ala Cys
                325                 330                 335

GCA ATT GGC TGC AAA GTA TAT ATT ACT GGG GGG CGG GGA TCA GAG AAC         1056
Ala Ile Gly Cys Lys Val Tyr Ile Thr Gly Gly Arg Gly Ser Glu Asn
            340                 345                 350

GGA GTC TCA AAA GAT GTC TGG GTT TAC GAT ACC CTG CAT GAG GAG TGG         1104
Gly Val Ser Lys Asp Val Trp Val Tyr Asp Thr Leu His Glu Glu Trp
        355                 360                 365

TCC AAG GCT GCC CCC ATG CTG GTG GCC AGG TTT GGC CAT GGA TCT GCT         1152
Ser Lys Ala Ala Pro Met Leu Val Ala Arg Phe Gly His Gly Ser Ala
370                 375                 380

GAA CTG AAG CAC TGC CTC TAT GTA GTC GGT GGG CAC ACA GCT GCA ACT         1200
Glu Leu Lys His Cys Leu Tyr Val Val Gly Gly His Thr Ala Ala Thr
                385                 390                 395                 400

GGC TGC CTC CCA GCC TCC CCC TCG GTC TCC CTA AAG CAA GTA GAA CAG         1248
Gly Cys Leu Pro Ala Ser Pro Ser Val Ser Leu Lys Gln Val Glu Gln
            405                 410                 415

TAT GAC CCC ACA ACC AAC AAA TGG ACC ATG GTA GCC CCA CTC CGC GAA         1296
Tyr Asp Pro Thr Thr Asn Lys Trp Thr Met Val Ala Pro Leu Arg Glu
        420                 425                 430
```

```
GGT GTC AGC AAT GCT GCT GTA GTG AGT GCC AAA CTT AAG CTG TTT GCT      1344
Gly Val Ser Asn Ala Ala Val Val Ser Ala Lys Leu Lys Leu Phe Ala
        435                 440                 445

TTC GGG GGT ACC AGT GTG AGC CAC GAC AAG CTG CCC AAG GTT CAG TGT      1392
Phe Gly Gly Thr Ser Val Ser His Asp Lys Leu Pro Lys Val Gln Cys
    450                 455                 460

TAC GAT CAA TGC GAG AAC AGA TGG TCA GTG CCG GCC ACC TGT CCC CAG      1440
Tyr Asp Gln Cys Glu Asn Arg Trp Ser Val Pro Ala Thr Cys Pro Gln
465                 470                 475                 480

CCC TGG CGT TAC ACA GCC GCA GCT GTG CTG GGA AAC CAG ATT TTT ATC      1488
Pro Trp Arg Tyr Thr Ala Ala Ala Val Leu Gly Asn Gln Ile Phe Ile
                485                 490                 495

ATG GGT GGA GAT ACA GAG TTC TCT GCC TGC TCC GCT TAC AAA TTC AAT      1536
Met Gly Gly Asp Thr Glu Phe Ser Ala Cys Ser Ala Tyr Lys Phe Asn
            500                 505                 510

AGT GAG ACT TAC CAG TGG ACC AAG GTG GGA GAT GTG ACA GCC AAG CGC      1584
Ser Glu Thr Tyr Gln Trp Thr Lys Val Gly Asp Val Thr Ala Lys Arg
        515                 520                 525

ATG AGC TGC CAC GCC GTG GCG TCC GGG AAC AAG CTT TAC GTA GTT GGA      1632
Met Ser Cys His Ala Val Ala Ser Gly Asn Lys Leu Tyr Val Val Gly
    530                 535                 540

GGG TAC TTC GGC ATT CAG CGC TGC AAG ACT TTG GAC TGT TAC GAC CCA      1680
Gly Tyr Phe Gly Ile Gln Arg Cys Lys Thr Leu Asp Cys Tyr Asp Pro
545                 550                 555                 560

ACT TTA GAT GTG TGG AAC AGC ATA ACC ACT GTT CCC TAC TCT CTG ATC      1728
Thr Leu Asp Val Trp Asn Ser Ile Thr Thr Val Pro Tyr Ser Leu Ile
                565                 570                 575

CCT ACT GCA TTC GTC AGC ACC TGG AAA CAC CTG CCT TCC TAA              1770
Pro Thr Ala Phe Val Ser Thr Trp Lys His Leu Pro Ser
            580                 585

(2) INFORMATION FOR SEQ ID NO:4:

(i) SEQUENCE CHARACTERISTICS:
        (A) LENGTH: 589 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Val Ser Val His Glu Asn Arg Lys Ser Arg Ala Ser Ser Gly
 1               5                  10                  15

Ser Ile Asn Ile Tyr Leu Phe His Lys Ser Ser Tyr Ala Asp Ser Val
                20                  25                  30

Leu Thr His Leu Asn Leu Leu Arg Gln Gln Arg Leu Phe Thr Asp Val
            35                  40                  45

Leu Leu His Ala Gly Asn Arg Thr Phe Pro Cys His Arg Ala Val Leu
        50                  55                  60

Ala Ala Cys Ser Arg Tyr Phe Glu Ala Met Phe Ser Gly Gly Leu Lys
65                  70                  75                  80

Glu Ser Gln Asp Ser Glu Val Asn Phe Asp Asn Ser Ile His Pro Glu
                85                  90                  95

Val Leu Glu Leu Leu Leu Asp Tyr Ala Tyr Ser Ser Arg Val Ile Ile
            100                 105                 110

Asn Glu Glu Asn Ala Glu Ser Leu Leu Glu Ala Gly Asp Met Leu Glu
        115                 120                 125

Phe Gln Asp Ile Arg Asp Ala Cys Ala Glu Phe Leu Glu Lys Asn Leu
    130                 135                 140
```

-continued

```
His Pro Thr Asn Cys Leu Gly Met Leu Leu Ser Asp Ala His Gln
145                 150                 155                 160

Cys Thr Lys Leu Tyr Glu Leu Ser Trp Arg Met Cys Leu Ser Asn Phe
            165                 170                 175

Gln Thr Ile Arg Lys Asn Glu Asp Phe Leu Gln Leu Pro Gln Asp Met
            180                 185                 190

Val Val Gln Leu Ser Ser Glu Glu Leu Glu Thr Glu Asp Glu Arg
        195                 200                 205

Leu Val Tyr Glu Ser Ala Met Asn Trp Ile Ser Tyr Asp Leu Lys Lys
        210                 215                 220

Arg Tyr Cys Tyr Leu Pro Glu Leu Leu Gln Thr Val Arg Leu Ala Leu
225                 230                 235                 240

Leu Pro Ala Ile Tyr Leu Met Glu Asn Val Ala Met Glu Glu Leu Ile
                245                 250                 255

Thr Lys Gln Arg Lys Ser Lys Glu Ile Val Glu Glu Ala Ile Arg Cys
            260                 265                 270

Lys Leu Lys Ile Leu Gln Asn Asp Gly Val Val Thr Ser Leu Cys Ala
            275                 280                 285

Arg Pro Arg Lys Thr Gly His Ala Leu Phe Leu Gly Gly Gln Thr
290                 295                 300

Phe Met Cys Asp Lys Leu Tyr Leu Val Asp Gln Lys Ala Lys Glu Ile
305                 310                 315                 320

Ile Pro Lys Ala Asp Ile Pro Ser Pro Arg Lys Glu Phe Ser Ala Cys
                325                 330                 335

Ala Ile Gly Cys Lys Val Tyr Ile Thr Gly Gly Arg Gly Ser Glu Asn
                340                 345                 350

Gly Val Ser Lys Asp Val Trp Val Tyr Asp Thr Leu His Glu Glu Trp
            355                 360                 365

Ser Lys Ala Ala Pro Met Leu Val Ala Arg Phe Gly His Gly Ser Ala
            370                 375                 380

Glu Leu Lys His Cys Leu Tyr Val Val Gly Gly His Thr Ala Ala Thr
385                 390                 395                 400

Gly Cys Leu Pro Ala Ser Pro Ser Val Ser Leu Lys Gln Val Glu Gln
                405                 410                 415

Tyr Asp Pro Thr Thr Asn Lys Trp Thr Met Val Ala Pro Leu Arg Glu
            420                 425                 430

Gly Val Ser Asn Ala Ala Val Val Ser Ala Lys Leu Lys Leu Phe Ala
            435                 440                 445

Phe Gly Gly Thr Ser Val Ser His Asp Lys Leu Pro Lys Val Gln Cys
    450                 455                 460

Tyr Asp Gln Cys Glu Asn Arg Trp Ser Val Pro Ala Thr Cys Pro Gln
465                 470                 475                 480

Pro Trp Arg Tyr Thr Ala Ala Val Leu Gly Asn Gln Ile Phe Ile
                485                 490                 495

Met Gly Gly Asp Thr Glu Phe Ser Ala Cys Ser Ala Tyr Lys Phe Asn
                500                 505                 510

Ser Glu Thr Tyr Gln Trp Thr Lys Val Gly Asp Val Thr Ala Lys Arg
            515                 520                 525

Met Ser Cys His Ala Val Ala Ser Gly Asn Lys Leu Tyr Val Val Gly
            530                 535                 540

Gly Tyr Phe Gly Ile Gln Arg Cys Lys Thr Leu Asp Cys Tyr Asp Pro
545                 550                 555                 560
```

```
-continued

Thr Leu Asp Val Trp Asn Ser Ile Thr Thr Val Pro Tyr Ser Leu Ile
            565                 570                 575

Pro Thr Ala Phe Val Ser Thr Trp Lys His Leu Pro Ser
            580                 585
```

NEURAL CELL PROTEIN MARKER RR/B AND DNA ENCODING THE SAME

This application is a divisional application of Ser. No. 08/317,305 filed on Oct. 3, 1994. The contents of all of the aforementioned application(s) are hereby incorporated by reference.

FIELD OF THE INVENTION

The invention relates to protein markers of neural tissue.

BACKGROUND OF THE INVENTION

A key to understanding the function of any tissue is the biochemical characterization of the proteins that are specific to that tissue. Mammalian neural tissue is composed of two predominant cell types, neurons and glia, which are organized into a great variety of structures. Whether neural tissue is viewed as one or several tissues, its organization involves many cells that are believed generally to perform the same physiological actions but at different places and in response to different signals. Accordingly, one can expect to find a large number of neural tissue-specific proteins in both undifferentiated and differentiated neural tissue, including those involved in both specialized and general processes.

Exemplary of specifiable neural tissue-specific proteins are: neuropeptide precursors, enzymes responsible for neurotransmitter synthesis and/or processing, and proteins that participate in the release, degradation or reuptake of neurotransmitters, signal receptor systems and ion channels. Proteins included in the basic cellular structures encompass those peculiar to neurons (axons, dendrites and synapses) and those involved in establishing specific cell-cell interactions. Also, there will be proteins involved in mental processes such as memory which are not at all yet understood at the cellular, let alone molecular level. Clearly, nervous system tissue is a difficult tissue to study at the molecular level due to its great complexity.

Mature mammalian neurons are incapable of cell division and cannot, with the exception of olfactory neurons, be generated from stem cells in the adult nervous system. Thus, continuous dividing clonal cell lines with neuronal characteristics have proven to be very useful to neurobiologists studying almost every aspect of the nervous system. Such cell lines allow the generation of large numbers of homogeneous cells and the manipulation of these cells through gene transfer to yield novel derivatives expressing foreign gene products. These advantages have led to development and characterization of a variety of neuronal cell lines, some of which have been useful for cellular, biochemical, and molecular studies. The utility of these different cell lines and their ability to approximate aspects of the neuronal phenotype vary widely. Rapidly dividing neuronal cell lines usually do not possess the phenotypic properties of terminally differentiated non-dividing neurons, instead they often resemble in vivo neuroblasts or embryonic neurons. For example, many rapidly dividing cell lines elaborate immature neurites with an immature cytoskeleton. Naturally occurring neoplastic derivatives of many neuronal cell types of the central (CNS) and peripheral (PNS) nervous systems usually fall within this category (e.g., neuroblastomas, pheochromocytomas and medulloblastomas).

It is presumed that all of the proteins of the nervous system are synthesized by translation from specific messenger RNA (mRNA) molecules, and thus each neural tissue-specific protein must have a corresponding mRNA. Thus, one approach to the study of the nervous system is through the transcription pattern of mRNA molecules, or by asking the question of what messenger RNA species neural tissue produces relative to its complete genomic potential. Estimates for the complexity of mammalian neural tissue-specific mRNAs are very high; tens to hundreds of thousands of discrete mRNA molecules are implicated in nervous system function (Bantle et al., Cell, 8, 39–150, 1976, and Hastie et al., Cell 9, 761–774, 1976), consistent with the variety of neural tissue-specific proteins listed above.

It is an object of the invention to provide a unique protein marker of neural tissue, and a nucleic acid encoding the protein.

Yet another object of the invention is to provide a novel protein marker of certain neuronal tumor cell lines.

Yet another object of the invention is to provide a novel protein marker of both neuroblastoma and glioblastoma cells.

Yet another object of the invention is to provide a novel protein marker of cells of both the central and peripheral nervous system.

Yet another object of the invention is to provide antibodies specific for a novel protein marker present on neural tissue.

Another object of the invention is to provide probes for detection of a novel protein marker, or its corresponding mRNA, that is more abundant in normal neural tissue than in neoplastic tissue.

SUMMARY OF THE INVENTION

The invention is based on the discovery of a novel protein, RR/B, that is detectable in neuronal cell lines derived from both central and peripheral nervous tissue, a nucleic acid sequence encoding RR/B, antibodies specific for RR/B, and methods for detection of RR/B or its coding nucleic acid.

Thus, in one aspect, the invention features an isolated DNA comprising the nucleotide sequence presented in SEQ ID NO: 1.

The invention also features an isolated DNA selected from the group consisting of: (a) an isolated DNA comprising a DNA sequence that encodes the amino acid sequence presented in SEQ ID NO: 2; and (b) an isolated DNA capable of hybridizing to the complement of a DNA according to (a) above under moderately stringent hybridization conditions and which encodes the amino acid sequence of SEQ ID NO: 2.

As used herein, the term "hybridization" refers to conventional DNA/DNA hybridization conditions. For example, for a probe of about 10–50 nucleotides, moderately stringent hybridization conditions are preferred and include 10× SSC, 5× Denhardts, 0.1% SDS, at 35–50 degrees for 15 hours; for a probe of about 50–300 nucleotides, "stringent" hybridization conditions are preferred and refer to hybridization in 6× SSC, 5× Denhardts, 0.1% SDS at 65 degrees for 15 hours.

The invention also encompasses recombinant expression vectors comprising a nucleic acid or isolated DNA encoding RR/B and a process for preparing RR/B, comprising culturing a suitable host cell comprising the vector under conditions suitable for promoting expression of RR/B, and recovering said RR/B.

The invention also features a nucleic acid probe comprising 10 consecutive nucleotides presented in SEQ ID NO: 1.

Preferably, the probe may comprise 15, 20, 50, 100, 200, and 300, etc., consecutive nucleotides presented in SEQ ID NO: 1.

In another aspect, the invention features a purified protein comprising an amino acid sequence encoded by DNA comprising the nucleotide sequence presented in SEQ ID NO: 1.

This aspect of the invention also encompasses a purified protein comprising the amino acid sequence encoded by DNA comprising a nucleotide sequence hybridizable under moderately stringent conditions to the nucleotide sequence presented in SEQ ID NO: 1.

The invention also features a synthetic polypeptide corresponding in amino acid residue sequence to at least a portion of the sequence of naturally occurring RR/B, and having a molecular weight equal to less than 60 kd. A synthetic polypeptide of the invention is useful for inducing the production of antibodies specific for the synthetic polypeptide and that bind to naturally occurring RR/B.

Preferred embodiments of this aspect of the invention include a group of synthetic polypeptides whose members correspond to a fragment of the RR/B protein comprising the sequence: S-S-E-E-L-E-T-E-D-E-R-L-V and K-Q-R-K-S-K-E-I-V-E-E-A-I.

The invention also features a monoclonal antibody specific for an epitope of RR/B, said RR/B comprising the amino acid sequence presented in SEQ ID NO: 2.

Preferably, the antibody is specific for an epitope specified by the amino acid residues 198 to 210 (S-S-E-E-L-E-T-E-D-E-R-L-V) (P1) or amino acid residues 258 to 270 (K-Q-R-K-S-K-E-I-V-E-E-A-I) (P2) of SEQ ID NO:2.

The invention also features a method of assaying for the presence of RR/B in a sample of mammalian cells, comprising the steps of: (a) providing an antibody specific for said RR/B; and (b) assaying for the presence of said RR/B by admixing an aliquot from a sample of said mammalian cells with said antibody under conditions sufficient to allow for formation and detection of an immune complex of said RR/B and said antibody. Such method is useful for detecting neural tissue versus most other tissue types of the body, as well as for detecting normal neural tissue versus neoplastic neural tissue.

Preferably, this method includes providing a monoclonal antibody specific for an epitope that is antigenically the same, as determined by Western blot assay, ELISA or immunocytochemical staining, and substantially corresponds in amino acid sequence to the amino acid sequence of a portion of said RR/B and having a molecular weight equal to less than that of said RR/B.

More preferably, the epitope comprises an amino acid sequence selected from the group consisting of: amino acid residues 198 to 210 (S-S-E-E-L-E-T-E-D-E-R-L-V) and amino acid residues 258 to 270 (K-Q-R-K-S-K-E-I-V-E-E-A-I) of SEQ ID NO:2.

The invention also features a method of assaying for the presence of RNA encoding RR/B in a sample of mammalian tissue as an indicator of the presence of neural tissue in said sample, comprising the steps of: (a) providing a nucleic acid probe hybridizable under moderately stringent conditions to RNA encoding the amino acid sequence of SEQ ID NO: 2; and (b) assaying for the presence of said RNA by admixing an aliquot from a sample of said mammalian tissue with said nucleic acid probe under conditions sufficient to allow detection of a hybrid formed between said nucleic acid probe and said RNA.

Preferably, the nucleic acid probe comprises a nucleotide sequence of 10, 15, 20, 50, 100, etc., consecutive nucleotides presented in SEQ ID NO: 1.

As used herein, "RR/B" refers to a 60 Kd protein having the -amino acid sequence presented in SEQ ID NO:2, that is present on both neuroblastoma and glioblastoma cells, and is not present on most other tissue types in the body (e.g., lung, liver, and heart tissues), and that is encoded by a messenger RNA that is present in at least 100-fold more abundance in non-neoplastic tissue or cells than in neoplastic tissue or cells. Therefore, the RR/B protein is useful as a marker that distinguishes neural tissue from most other tissue types, and that distinguishes non-neoplastic tissue from neoplastic tissue. Because RR/B is present on both neuroblastoma and glioblastoma cells, RR/B is a protein marker that may appear on neural cells prior to the developmental branch point that heralds the emergence of the two types of cells.

The invention thus also features a kit for detecting RR/B, the kit including at least one package containing an antibody or idiotype-containing polyamide portion of an antibody raised to a synthetic polypeptide of this invention or to a conjugate of that polypeptide bound to a carrier. An indicating group or label is utilized to indicate the formation of an immune reaction between the antibody and RR/B when the antibody is admixed with neural tissue or cells.

This aspect of the invention also features a kit for detection RNA encoding RR/B including at least one package containing a nucleic acid probe of at least 15 nucleotides that is hybridizable under moderate or stringent conditions to RNA encoding RR/B.

A diagnostic reagent that binds to neural tissue comprises yet another embodiment of the present invention. This reagent is an antibody that can be linked to an indicating group. The antibody or idiotype-containing portion of an antibody raised to a synthetic polypeptide or conjugate of that synthetic polypeptide bound to a carrier. An immune reaction is formed when the antibody is admixed with neural cell tissue that includes RR/B. The indicating group bound to the antibody or as an exogenously supplied reagent indicates the formation of an immune reaction between the antibody and neural tissue containing RR/B.

This aspect of the invention is the provision of a diagnostic system for assaying the presence of a naturally occurring amino acid residue sequence of a protein present in the neural cells, and of an antibody that immunologically reacts with neural cell tissues that include particular amino acid sequences.

Further features will become more fully apparent in the following description of the embodiments of this invention and from the appended claims.

BRIEF DESCRIPTION OF THE DRAWINGS

In the drawings:

FIG. 1A is the cDNA sequence of human RR/B cDNA (SEQ ID NO:1).

FIG. 1B is the predicted amino acid sequence of human RR/B (SEQ ID NO:2).

FIG. 2 is the DNA sequence of murine brain RR/B cDNA (SEQ ID NO:3).

FIG. 3 is the predicted amino acid sequence of murine RR/B (SEQ ID NO:4).

FIG. 4 is a comparison of the nucleotide sequences of human and murine RR/B. The top sequence is the human RR/B nucleotide sequence (SEQ ID NO:1), the middle sequence is the mouse RR/B nucleotide sequence (SEQ ID NO:3), and the bottom sequence demonstrates a consensus overlap between the human and mouse RR/B nucleotide sequences. Areas with a difference in the nucleotide sequence are represented by dashes.

FIG. 5 is a comparison of the predicted amino acid sequences of human (SEQ ID NO:2; top) and murine (SEQ ID NO:4; bottom) RR/B.

DETAILED DESCRIPTION OF THE INVENTION

Figure 6A:
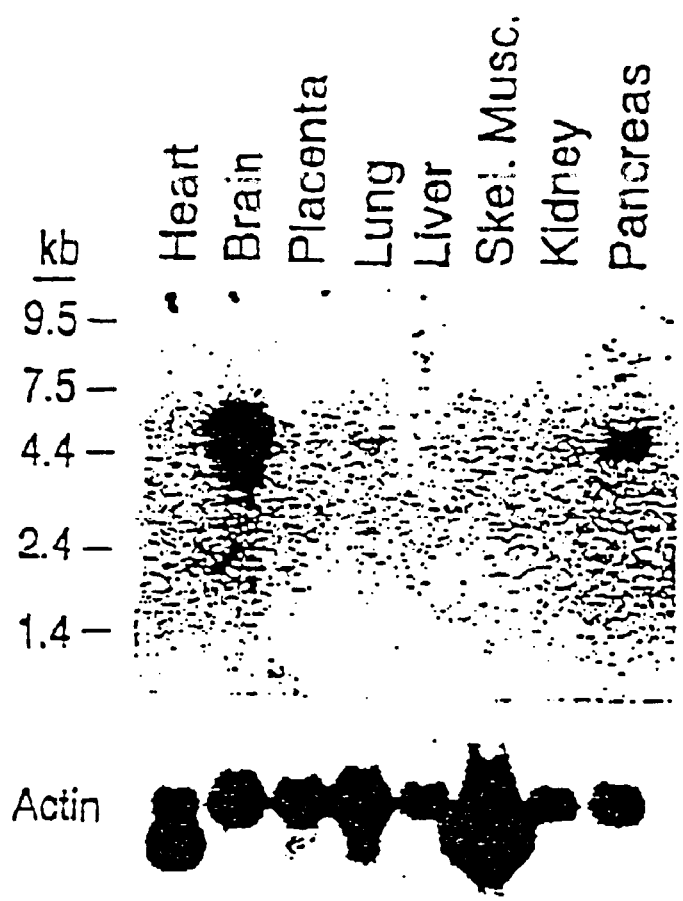
FIG. 6A is a Northern blot analysis of RR/B mRNA in human adult tissues.

The present invention contemplates the novel neural cell protein marker RR/B, cDNA encoding RR/B, nucleic acid probes for detection of mRNA encoding RR/B, and synthetic polypeptides whose sequences correspond to a portion of RR/B and have a molecular weight equal to less than that of the 60 kd RR/B.

RR/B is present abundantly in cells or cell lines of neural origin and megarkaryocytes relative to other cell types. This is in contradistinction to proteins such as somatostatin, thyrotropin-releasing factor (TRF), luteinizing hormone-releasing factor (LRF), the endorphins and enkephalins, or the several other small polypeptides such as bombesin, caerulein or physalamine that have been found to occur in the brain as well as in other tissues of the animal body. (Guillemin, Science 202, 390–402 (1978)).

The term "RR/B" is used herein to refer to the 60 kd direct polypeptide translation product of a messenger RNA having a complementary DNA sequence of SEQ ID NO:1.

The phrase "RR/B derivative" is used herein to mean the polypeptide-containing material that results from cellular processing of RR/B. Thus, an RR/B derivative may therefore be a protein cleavage product of RR/B.

The phrase "immune reaction" is used herein to mean the binding of a ligand with its receptor and includes the binding between an antigen (ligand) with an antibody (receptor) as well as between an antigen and an idiotype-containing polyamide portion of an antibody (receptor). Similarly, "immune complex" refers to a complex consisting of the receptor (antibody) bound to its cognate antigen.

The phrase "corresponds substantially" as used herein in conjunction with amino acid sequences means that the amino acid sequence of a first polypeptide is sufficiently similar to the amino acid sequence contained in a second polypeptide so that antibodies to the first polypeptide (e.g. synthetic polypeptide) form an immune reaction with the second polypeptide (e.g. RR/B or RR/B derivative) when admixed in an aqueous medium. The preparation of such polypeptides and antibodies are discussed hereinafter.

The epitope-containing amino acid sequence portions of the above two polypeptides, e.g. synthetic polypeptide and RR/B protein, are most preferably identical, but conservative changes in amino acid residues and deletions or additions of amino acid residues within the epitope may be made and still permit the cross-reaction of an antibody to the first polypeptide with the second polypeptide, as is known. Conservative amino acid changes are well known, and include exchanges of residues such as between lysine and arginine, between aspartic acid and glutamic acid, between leucine and isoleucine, and between aspartic acid and glutamic acid, between leucine and isoleucine, and the like.

EXAMPLE I

The nucleotide sequences encoding human RR/B and mouse RR/B are presented in SEQ ID NOS: 1 and 3, respectively, corresponding to FIGS. 1 and 2, respectively.

Murine RR/B was cloned using 2.0 Kb of human RR/B cDNA as a probe to screen a mouse brain cDNA library under low stringency; about 15 clones were isolated. The nucleotide sequences of murine RR/B partial cDNA clones are shown in FIG. 2, with 90% nucleotide sequence homology to human RR/B (FIG. 4). In FIG. 4, the top sequence is the human RR/B nucleotide sequence (SEQ ID NO:1), the middle sequence is the mouse RR/B nucleotide sequence (SEQ ID NO:3), and the bottom sequence demonstrates a consensus overlap between the human and mouse RR/B nucleotide sequences. Areas with a difference in the nucleotide sequence are represented by dashes. Interestingly, the homology of the deduced amino acids between these two species is more than 99% (FIG. 5). These results indicate that RR/B is a highly conserved gene in the human and mouse which might indicate an important role in cell-cell communication.

The homology of RR/B with the ring canal kelch gene is 28% between amino acid residues 562 to 1329. Lower homology of RR/B with other genes such as Vaccinia Virus A55R protein was found to be about 23% between amino acid 589 to 942. The homology of RR/B with the ring cell kelch gene at the nucleotide level is ~50% between nucleotide residues 577 to 2000.

Nucleic acid probes corresponding to portions of the sequence of human or mouse RR/B may be made according to conventional DNA synthesis techniques, and may be any length sufficient to allow formation of a stable hybrid, e.g., 10, 20, 50, 100, 300, etc., bases in length.

EXAMPLE II

The human and mouse RR/B amino acid sequences are presented in SEQ ID NOS: 2 and 4, respectively, and the sequences are compared in FIG. 5.
Synthetic Polypeptides A synthetic polypeptide of the invention corresponds in amino acid sequence to at least a portion of the sequence of RR/B. Exemplary of such synthetic polypeptides are two synthetic polypeptides P1 and P2, discussed hereinbefore. That previous discussion illustrated chat the sequences of the synthetic polypeptides corresponded substantially to portions of the sequences of the proteins translated by the cell from the cDNA sequence encoding RR/B shown in FIG. 1, and that the molecular weights of the synthetic polypeptides are substantially less than the molecular weight of RR/B itself.

EXAMPLE III

Interference with RR/B Synthesis using Antisense Oligonucleotides

Figure 10:
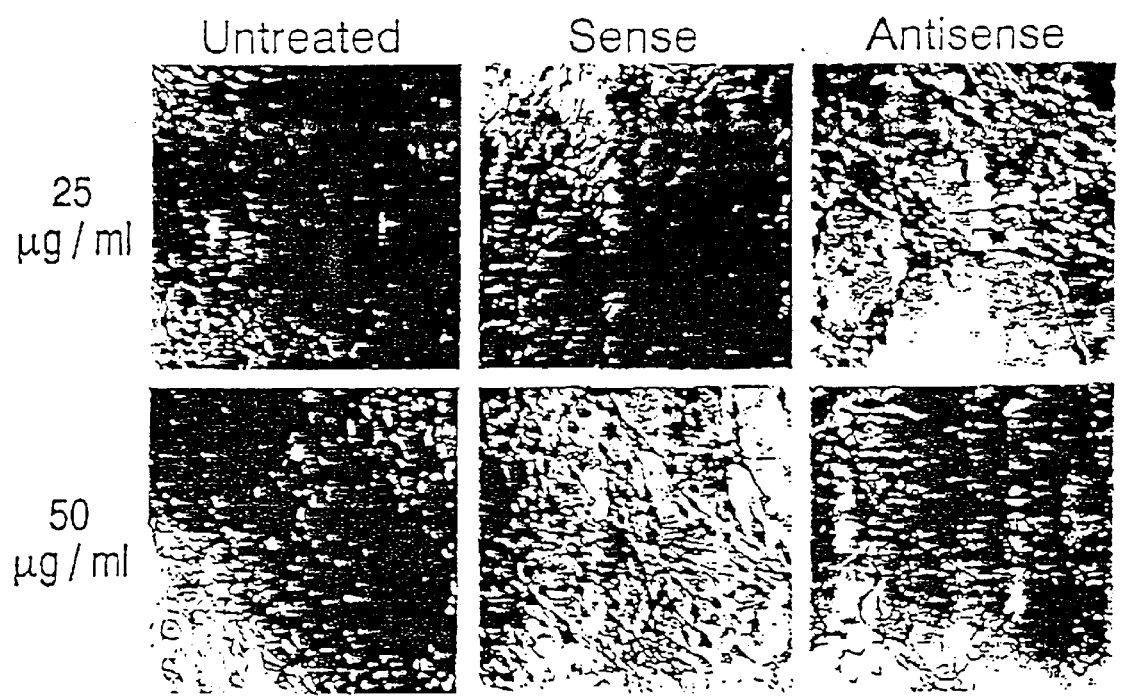
FIG. 10 is an autoradiogram of cultures having been treated with antisense RR/B oligonucleotides on cell-cell interactions and cell attachment. U373 cells were exposed to RR/B sense or antisense oligonucleotide 1B (corresponding to 211 nt–226 nt), at the indicated concentrations for 24 h and then assayed for [$^3$H]-thymidine incorporation, viability and morphological changes.

In an effort to determine the role of RR/B in brain, we examined the effects of blocking synthesis of RR/B proteins by RR/B antisense oligonucleotides on cell-cell interactions. Brain cell lines of glioblastomal U373 cells were treated with human RR/B sense or antisense phophorothiol oligonucleotides for 24 hr or 48 hr. Inhibition of glial cell-cell connections and also attachment of glial cells to plate matrix following RR/B antisense oligonucleotides treatment was observed (FIG. 10). U373 cells treated with antisense oligonucleotide 1B (corresponding to second amino acid to the eight amino acid), resulted in detachment and aggregation of cells compared to the attached and adherent monolayer of U373 cells untreated or treated with sense oligonucleotide 1B. These results indicate that RR/B may be involved in cell attachment to plate matrix and cell-cell interactions.

EXAMPLE IV

Figure 6B:
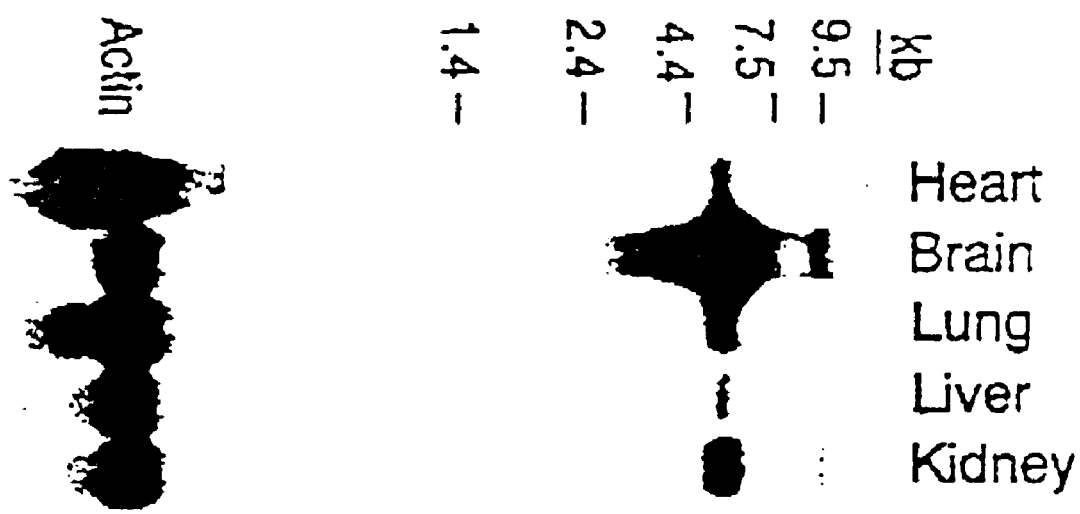
FIG. 6B is a Northern blot analysis of RR/B mRNA in human fetal tissues.
Figure 7:
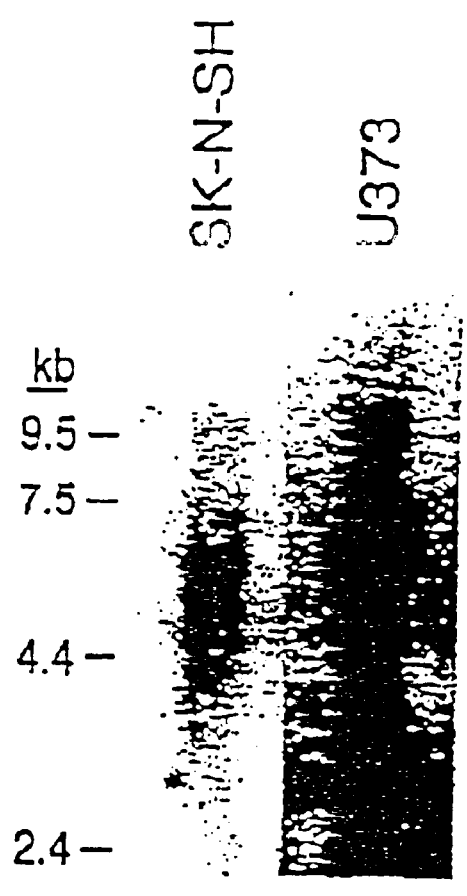
FIG. 7 is a Northern blot analysis of RR/B mRNA in glioblastoma and neuroblastoma cell lines.
Figure 8A:
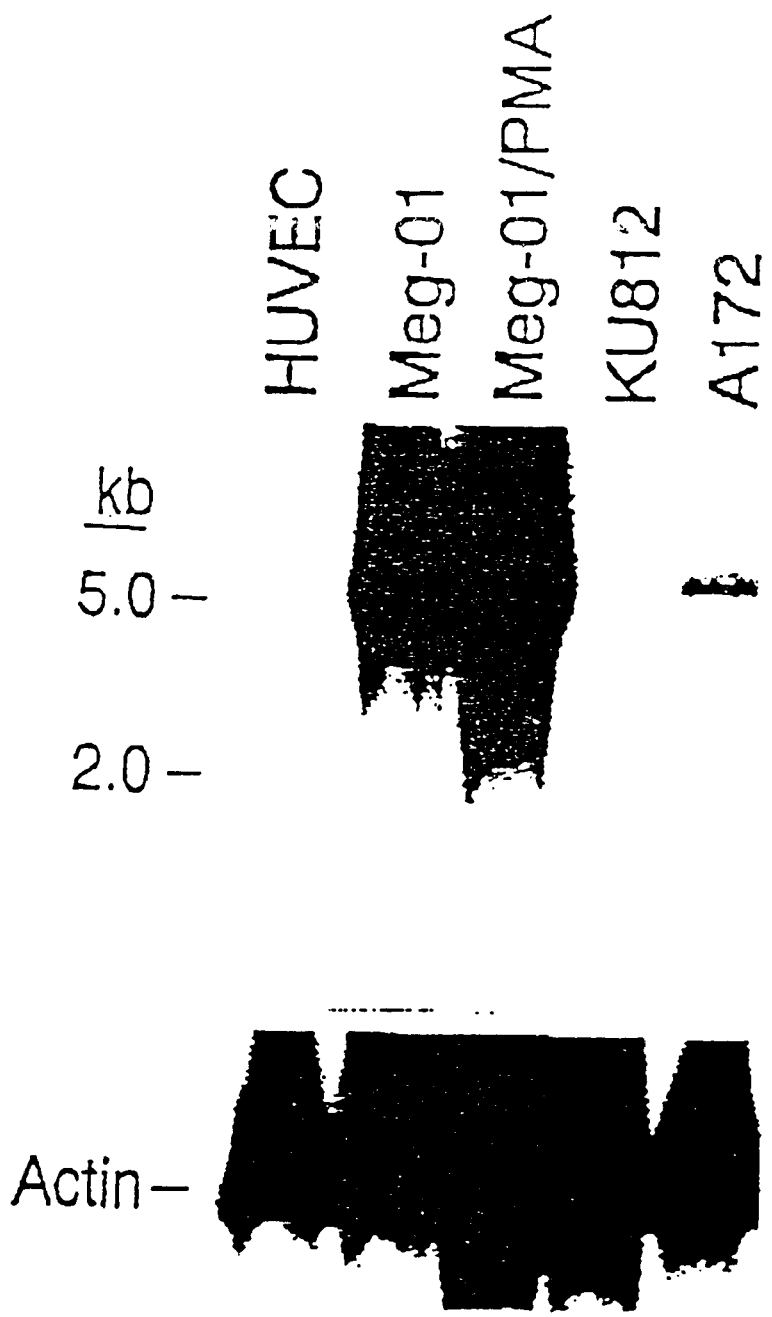
FIG. 8A is a Northern blot of RR/B mRNA in permanent megakaryocytic cell lines.
Figure 8B:
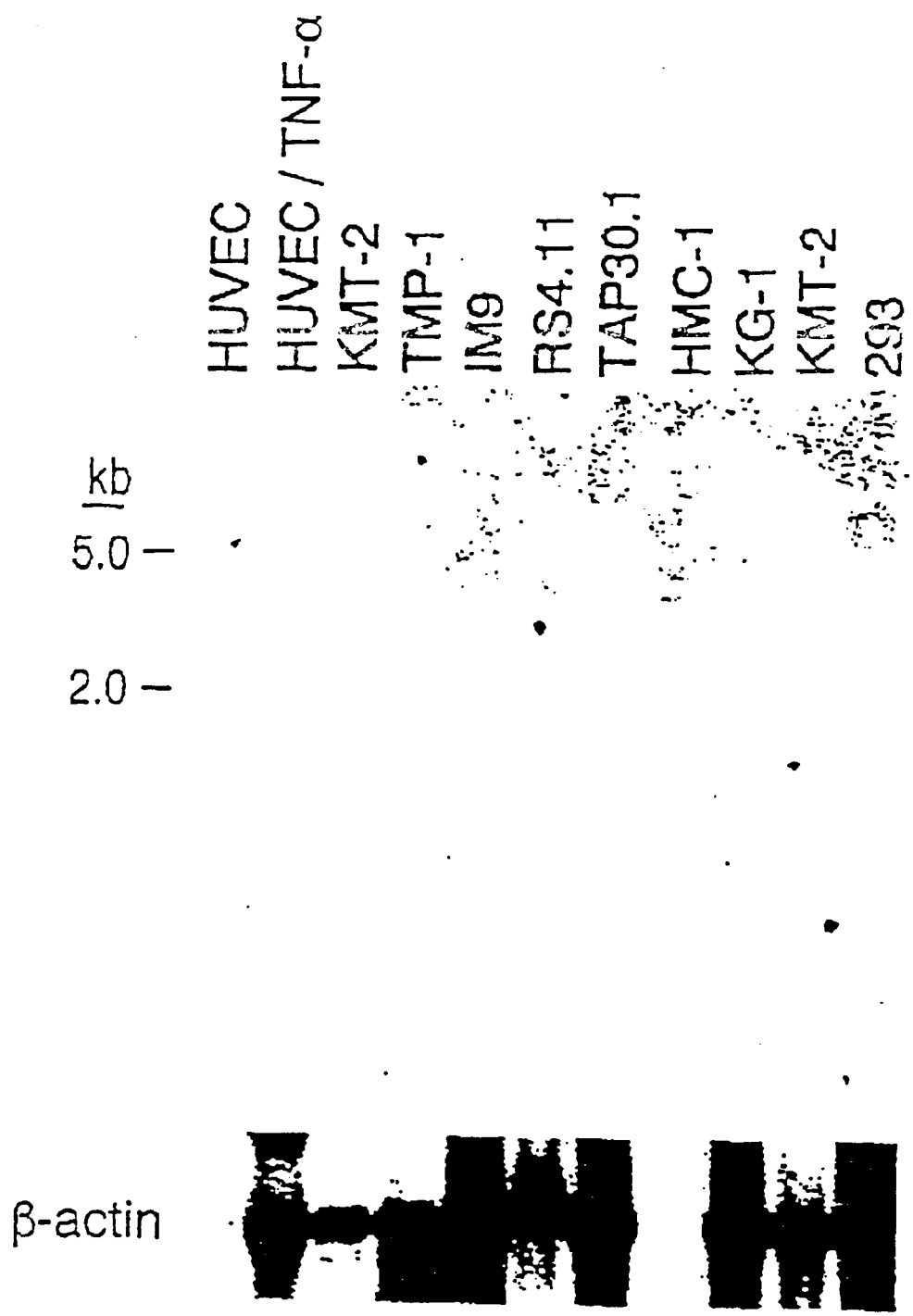
FIG. 8B is a Northern blot of RR/B mRNA in various permanent human cell lines.

A nucleic acid probe corresponding to residues 1351–1440 of the human RR/B nucleic acid sequence (SEQ ID NO: 1) was used to survey human cells lines and tissues for the presence of RR/B mRNA using Northern blot analysis. The results, presented in FIG. 6, revealed that RR/B mRNA is approximately 5.5 Kb and is highly expressed in human adult brain tissue (FIG. 6A). Interestingly, RR/B mRNA is expressed with about 50-fold greater abundance in human fetal brain tissue relative to human adult brain tissue or any other tissue analyzed. A low level of RR/B mRNA expression was found in adult pancreatic tissue, and a low level of RR/B mRNA expression was found in fetal kidney (FIG. 6B). RR/B mRNA was also detectable in brain cell lines of glioblastoma (U373 cell line) and neuroblastoma (SK-N-SH cell line) origin (FIG. 7), as well as in megakaryocytice cell lines (FIG. 8A). RR/B mRNA was not detected in various non-hematopoietic cell lines (FIGS. 8A and B).

Figure 9:
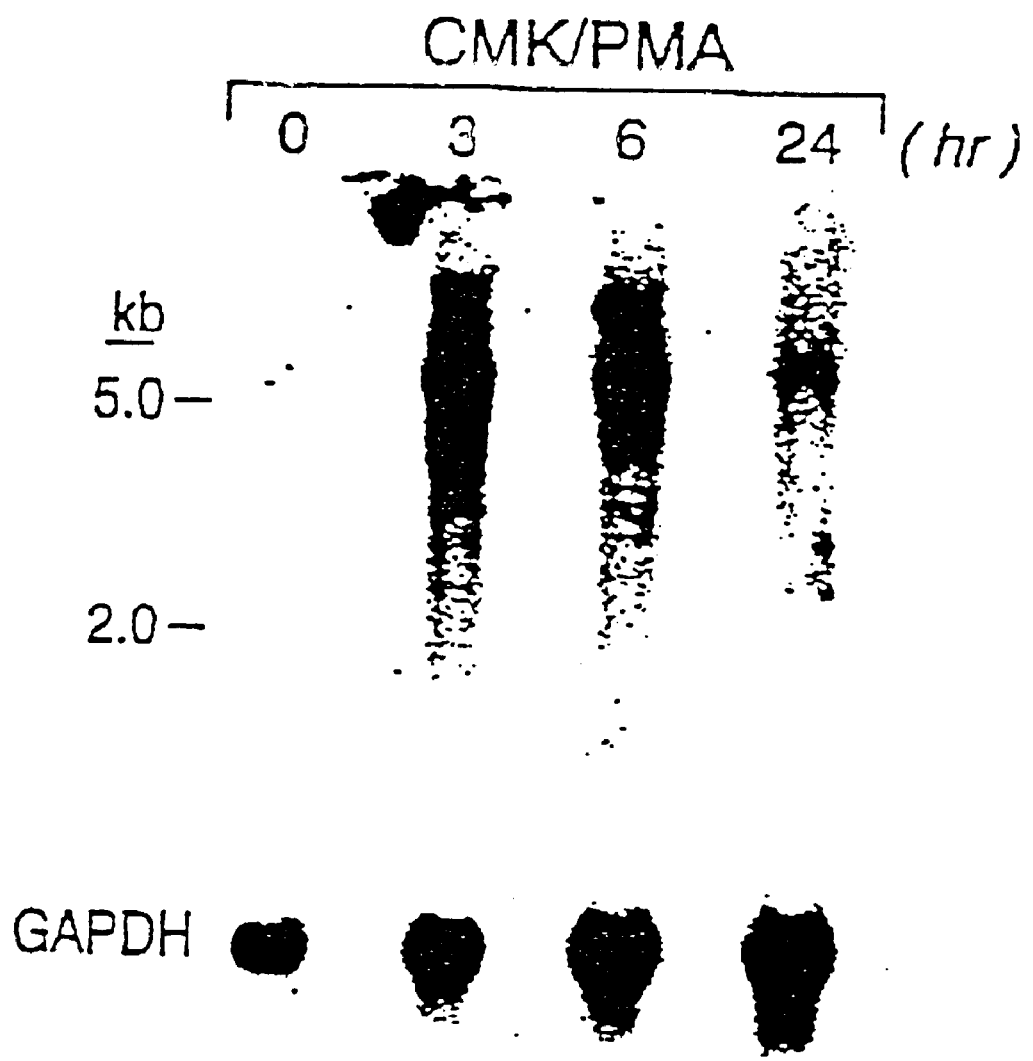
FIG. 9 is a Northern blot of human RR/B mRNA in the presence of PMA in permanent CMK cell line.

Expression of RR/B was found to be upregulated by PMA (phorbol 12-myristate 13-acetate) (FIG. 9). Kinetic analysis of RR/B expression in CMK megakaryocytic cell lines induced to differentiate in vitro by PMA for 3, 6, or 24 hr, revealed upregulation of RR/B expression after 3 hr and 6 hr followed by downregulation of RR/B after 24 hr.
Northern Blot Analysis.

Poly (A)(+) mRNA samples (usually 2 micrograms) were fractionated by electrophoresis on 1.5 percent agarose gels in the presence of 1 molar formaldehyde as described in Rave et al., Nucleic Acids Res., 6, 3559–3567 (1979) and transferred to nitrocellulose as described in Thomas P. S., Proc. Natl. Acad. Sci. U.S.A., 77, 5201–5205 (1980). The blots were prehybridized overnight at 42 degrees C. in 50 percent formamide, 0.75 molar NaCl, 25 millimolar PIPES [1,4-piperazine-bis-(2-ethanesulfonic acid)], pH 6.8, 0.2 percent sodium dodecyl sulfate (SDS), 25 millimolar EDTA, 100 micrograms per milliliter salmon sperm DNA, 100 micrograms per milliliter yeast mRNA and 5×Denhardt's solution as described in Denhardt, D., Biochem. Biophys. Res. Comm., 23, 641–646 (1966). The blots were then hybridized overnight with $^{32}$P-labeled probes at 42 degrees C. in the same medium but the 1×Denhardt's solution.

One-quarter or one-eighth of each crude plasmid extract or (for followup screening) 100 nanograms of purified super-coiled plasmid were labeled with $^{32}$P by random primed as described in Feinberg, et al., Anal. Biochem. 132:6–13 (1983) to specific activities of 2–4×10$^8$ counts per minute per microgram. Blots were washed in two changes of 2×SSC standard sodium citrate solution; 30 millimoles trisodium citrate and 0.3 molar sodium chloride at pH 7.0) 0.2 percent SDS for 60 minutes each at 42 degrees C. and once in 0.1×percent SSC (1.5 millimolar trisodium citrate and 15 millimolar sodium chloride at pH 7.0), 0.2 percent SDS for 15 minutes at 67 degrees C. The washed blots were then exposed to is Kodak XRP-5 or XAR-1 X-ray film at minus 50 degrees C. using Cronex Lightening Plus intensification screens for 1 hr. to 4 days. Size estimates were based on comparisons with plasmid λ-HindIII standards.

EXAMPLE V
Antigenic Peptides

Two 13-residue synthetic polypeptides corresponding to two amino acid residue sequences within the RR/B open reading frame were chemically synthesized to aid in detection of RR/B.

Other synthetic polypeptides of the invention will be useful as antigenic peptides for generation of antibodies specific for RR/B provided they possess the following characteristics. The peptide will include a minimum of 12 and preferably 15 amino acid residues, and an optimum length of 20–21 amino acids. The hydrophilicity and antigenic index of the amino acid sequence of RR/B may be determined by Analytical Biotechnology Sciences, Boston, Mass., using computer programming. For example, additional potential synthetic peptides useful according to the invention include the group comprising amino acid residues 294–307, 175–186, 351–371 and 412–429 of FIG. 1 (SEQ ID NO: 2).

The amino acid sequences of the polypeptides were searched in a computer database to preclude the possibility that at reasonable concentrations, antisera to any of these polypeptides would specifically interact with any protein of a known sequence. Neither of the polypeptides were found to have a close homolog.

Antisera to the polypeptide-carrier conjugates were raised in rabbits. The sera were shown to react strongly with the appropriate polypeptides by ELISA following the procedures of Green et al., Cell, 28, 477–487 (1982).

The antisera may then be used to probe extracts of $^{35}$S-methionine labeled cells, as described below. Antisera to synthetic polypeptides P1 and P2 were found to react with a protein with a gel mobility of about 60K daltons.

The amino acid residue sequence of synthetic polypeptides P1 and P2 are as represented by the formulas below, from left to right and in the direction from amino-terminus to carboxy-terminus, using conventional single letter code for amino acid residues:

EXAMPLE VI
Preparation of Antibodies

The peptide ABCP-51 (P1) corresponding to amino acid residues 198 to 210 and ABCP-52 (P2) corresponding to amino acid residues 258 to 270 for the human and mouse RR-B proteins were synthesized. Coupling of the peptide to carrier protein and immunizations was performed as described (Dymecki, S. M., supra). Rabbit antibodies against this peptide were raised and sera were titered against peptide antigen by ELISA. The sera exhibiting the highest titer (1:27,000) were used in subsequent experiments.

Techniques for preparing monoclonal antibodies are well known, and monoclonal antibodies of this invention may be prepared by using the synthetic polypeptides of this invention, preferably bound to a carrier, as the immunogen as was done by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic polypeptides of this invention or their conjugates with a carrier.

Antibodies are utilized along with an "indicating group" also sometimes referred to as a "label". The indicating group or label is utilized in conjunction with the antibody as a means for determining whether an immune reaction has taken place, and in some instances for determining the extent of such a reaction.

The indicating group may be a single atom as in the case of radioactive elements such as iodine 125 or 131, hydrogen 3 or sulfur 35, or NMR-active elements such as fluorine 19 or nitrogen 15. The indicating group may also be a molecule such as a fluorescent dye like fluorescein, or an enzyme, such as horseradish peroxidase (HRP), or the like.

The terms "indicating group" or "label" are used herein to include single atoms and molecules that are linked to the antibody or used separately, and whether those atoms or molecules are used alone or in conjunction with additional reagents. Such indicating groups or labels are themselves well-known in immunochemistry and constitute a part of this invention only insofar as they are utilized with otherwise novel antibodies, methods and/or systems.

EXAMPLE VII

Detection of RR/B and Subcellular Localization

Another embodiment of this invention relates to an assay for the presence of RR/B. Here, an above-described antibody is raised and harvested. The antibody or idiotype-containing polyamide portion thereof is then admixed with candidate tissue and an indicating group. The presence of the naturally occurring amino acid sequence is ascertained by the formation of an immune reaction as signaled by the indicating group. Candidate tissues include any tissue or cell line or bodily fluid to be tested for the presence of RR/B.

The expression of the RR-B gene product was investigated using and antiserum prepared in rabbits against two peptides as described above.

The CMK cells or U3T3 cells were metabolically labeled with $^{35}$S-methionine and extracts were immunoprecipitated with anti-RR-B antiserum. A major protein species of 60 kd was detected in CMK and U3T3 cells. RR-B protein was localized in the membrane with some of the protein found in the cytoplasm, by Western blot analysis of the nuclear membrane and cytoplasmic fractions, as generally described in Towbin et al., Proc. Natl. Acad. Sci. U.S.A., 76, 4350–4354 (1979). This localization for RR-B was confirmed by immunofluorescence analysis to be associated mainly with the plasma membrane.

Metabolic labeling immunoprecipitation, and immunolocalization assays were performed in CMK and U373 cells as described previously (Furth, M. E., et al., Oncogene 1:47–58, 1987; Laemmli, U. K., Nature 227:680–685, 1970; Yarden, Y., et al., EMBO J. 6:3341–3351, 1987; Konopka, J. B., et al., Mol. Cell. Biol. 5:3116–3123, 1985). For immunoblot analysis, total lysates were prepared (using Fruth's lysis buffer) (Fruth, M. E., et al., Oncogene, 1:47–58, 1987). Relative protein concentrations were determined with a colorimetric assay kit (Bio-Rad) with bovine serum albumin as the standard. A protein of lysate containing approximately 0.05 mg of protein was mixed with an equal volume of 2×SDS sample buffer containing 2 mercaptoethanol, boiled for 5 min., fractioned on 10% polyacrylamide-SDS gels (Konopka, J. B., et al., J.Virol., 51:223– 232, 1984) and transferred to immunobilon polyvinyldine difluoride (Millipore Corp., Bedford, Mass.) filters. Protein blots were treated with specific antipeptide antibodies (see below). Primary binding of the RR-B-specific antibodies was detected using anti-IgG second antibodies conjugated to horseradish peroxidase and subsequent chemiluminescence development ECL Western blotting system (Amersham International).

For metabolic labeling, $10^6$ cells were labeled with 100 $\mu$Ci of $^{35}$S-methionine in 1 ml of Dulbecco's modified Eagles medium minus methionine (Amersham Corp.) for 16 h. Immunoprecipitation of RR-B protein form labeled cells with antipeptide antiserum was performed as described (Dymecki, S. M., et al., J. Biol. Chem 267:4815–4823, 1992). Portions of lysates containing $10^7$ cpm of acid-insoluble $^{35}$S-methionine were incubated with 1 $\mu$g of the antiserum in 0.5 ml of reaction mixture. Immunoprecipitation samples were analyzed by SDS-polylarcylamide gel electrophoresis and autoradiography.

For immunolocalization studies, $10^7$ CMK cells were resuspended in 1 ml of sonication buffer (60 mM Tris-HCl, pH 7.5, 6 mM EDTA, 15 mM EGTA, 0.75M sucrose, 0.03% leupeptin 12 mM phenylmethylsulfonyl fluoride, 30 mM 2-mercaptoethanol). Cells were sonicated 6 times for 10 seconds each and centrifuged at 25,000×g for 10 min at 4° C. The pellet was dissolved in 1 ml of sonication buffer and centrifuged at 25,000×g for 10 min at 4° C.

The pellet (nucleus fraction) was resuspended in 1 ml of sonication buffer and added to an equal volume of 2×SDS sample buffer. The supernatant obtained above (after the first sonication) was again centrifuged at 100,000×g for 40 min at 4° C. The supernatant (cytosolic fraction) was removed and added to an equal volume of 2×concentrated SDS sample buffer. The remaining pellet (membrane fraction) was washed and dissolved in sonication buffer and SDS sample buffer as described above. Protein samples were analyzed by electrophoresis on 10% polyacrylamide gels, according to the Laemmli method (Konopka, J. B., supra). The proteins were transferred from the gels on a 0.45-$\mu$m plyvinylidine difluoride membrane for subsequent immunoblot analysis. Primary binding of the RR-B specific antibodies was detected using anti-IgG second antibodies conjugated to horseradish peroxidase.

For immunohistochemical localization of RR-B protein, CMK cells or U3T3 were grown on cover slips to approximately 50% confluence and were washed with PBS (pH 7.4) after removing the medium. The cells were prefixed for 1 min at 37° C. in 1% paraformaldehyde containing 0.075% Triton X-100, rinsed with PBS and then fixed for 10 min with 4% paraformaldehyde. After the fixation step, cells were rinsed in PBS, quenched in PBS with 0.1 and finally rinsed again in PBS. For antibody staining, the cells were first blocked with a blocking solution (3% bovine serum albumin in PBS) and incubated for 1 h at 37° C. The cells were then incubated for 1 h at 37° C. with antiserum (1:100 dilution or with preimmune rabbit serum (1:100) (see below). After the incubation with the primary antibody, the cells were washed in PBS containing 3% bovine and serum albumin and 0.1% Tween 20 and incubated for 1 h at 37 C. in fluorescein-conjugated donkey anti-rabbit IgGs (Jackson Immunoresearch, Maine) diluted 1:100 in blocking solution.

The coverslips were washed in PBS (pH 8.0), and glycerol was added to each coverslip before mounting on glass slides and sealing with clear nail polish. All glass slides were examined with a Zeiss Axiophot microscope.

EXAMPLE VIII

The above methods for detection of RR/B protein or nucleic acid are applicable to analyses involving tissues, cell lines and bodily fluids suspected of containing the RR/B marker.

For example, a sample of brain tissue suspected of possessing neoplastic properties may be analyzed. Neoplastic tissue typically contains lower levels of RR/B relative to non-neoplastic tissue.

An aliquot of the suspect sample and a non-neoplastic control sample are provided and admixed with an effective amount of an antibody specific for RR/B, as herein described, and an indicating group. The admixture is typically incubated, as is known, for a time sufficient to permit an immune reaction to occur. The incubated admixture is then assayed for the presence of an immune reaction as indicated by the indicating group. The relative levels of RR/B in the suspect sample and the control sample are then compared, allowing for diagnosis of a neoplastic or non-neoplastic state in the suspect sample.

Alternatively, where RR/B is a normal constituent of a tissue, e.g., human brain tissue, detection of RR/B may be used to determine the neural or non-neural origin of the tissue. In this respect, the level of RR/B is measured in a suspect tissue and compared to the amount present relative to human brain tissue. A comparable level of RR/B will indicate neural origin of the suspect tissue, whereas a relatively low level of RR/B in the suspect tissue will usually indicate that the suspect tissue is of non-neural origin.

The above types of analyses for the presence of RR/B may, of course, be performed using analysis for RR/B mRNA, e.g., via Northern blot or RNA dot blot analyses, both of which are conventional and known in the art.

A diagnostic system, preferably in kit form, comprises yet another embodiment of this invention. This system is useful for assaying the presence of RR/B or its derivative in brain cells by the formation of an immune complex. This system includes at least one package that contains an antibody of this invention.

An indicating group or label is preferably supplied along with the antibody and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

We claim:

1. An isolated DNA comprising the nucleotide sequence presented in SEQ ID NO: 1.

2. An isolated DNA comprising a DNA sequence that encodes the amino acid sequence present in SEQ ID NO:2.

3. A recombinant expression vector comprising a DNA according to claim 1 or 2.

4. A process for preparing a protein comprising the amino acid sequence of SEQ ID NO:2, comprising culturing a suitable host cell comprising a vector aaccording to claim 3 under conditions suitable for promoting expression of said protein, and recovering said protein.

5. A method of assaying for the presence of RNA encoding RR/B in a sample of mammalian tissue, comprising the steps of:

(a) providing a nucleic acid probe which specifically hybridizes to RNA encoding the amino acid sequence of SEQ ID NO: 2; and (b) assaying for the presence of said RNA by admixing an aliquot of RNA isolated from a sample of said mammalian tissue, with said nucleic acid probe under conditions sufficient to allow formation of a hybrid between said nucleic acid probe and said RNA aliquot and detecting said hybrid formation wherein the presence of hybrid formation indicates the presence of RNA encoding RR/B in the sample of the mammalian tissue.

6. The method of claim 5 wherein said nucleic acid probe comprises a nucleotide sequence of 10 consecutive nucleotides presented in SEQ ID NO: 1.

7. The method of claim 6 wherein said nucleic acid probe comprises a nucleotide sequence of 15 consecutive nucleotides presented in SEQ ID NO: 1.

8. The method of claim 7 wherein said nucleic acid probe comprises a nucleotide sequence of 20 consecutive nucleotides presented in SEQ ID NO: 1.

* * * * *